(12) United States Patent
Ito et al.

(10) Patent No.: US 8,741,803 B2
(45) Date of Patent: Jun. 3, 2014

(54) PESTICIDAL COMPOSITION AND METHOD FOR CONTROLLING PEST

(75) Inventors: Yoshihiro Ito, Tokyo (JP); Yuki Nakano, Tokyo (JP)

(73) Assignees: Kumiai Chemical Industry Co., Ltd., Tokyo (JP); Ihara Chemical Industry Co., Ltd., Tokyo (JP)

( * ) Notice: Subject to any disclaimer, the term of this patent is extended or adjusted under 35 U.S.C. 154(b) by 356 days.

(21) Appl. No.: 12/673,268

(22) PCT Filed: Jul. 31, 2008

(86) PCT No.: PCT/JP2008/063800
§ 371 (c)(1),
(2), (4) Date: Feb. 12, 2010

(87) PCT Pub. No.: WO2009/022548
PCT Pub. Date: Feb. 19, 2009

(65) Prior Publication Data
US 2011/0067612 A1   Mar. 24, 2011

(30) Foreign Application Priority Data
Aug. 10, 2007   (JP) .................. 2007-209387

(51) Int. Cl.
A01N 43/40   (2006.01)
A01N 43/653   (2006.01)
A01P 7/00   (2006.01)
A01P 7/02   (2006.01)
A01P 7/04   (2006.01)

(52) U.S. Cl.
USPC ............ 504/100; 514/355; 514/383; 514/384

(58) Field of Classification Search
USPC .................. 504/100; 514/355, 383
See application file for complete search history.

(56) References Cited

U.S. PATENT DOCUMENTS 5,360,806 A * 11/1994 Toki et al. ............... 514/318

FOREIGN PATENT DOCUMENTS

| EP | 1803712 | * | 7/2007 |
| JP | 2000 198768 | | 7/2000 |
| WO | 2006 043635 | | 4/2006 |

OTHER PUBLICATIONS

CABA abstract 2001:25047 (2001).*
"The Pesticide Manual", 13$^{th}$ Edition, British Crop Council (2003).
"Shibuya Index", 11$^{th}$ Edition, published by Shibuya Index Research Association (2006).
"Shibuya Index", 10$^{th}$ Edition, published by Shibuya Index Research Association (2005).
"Monthly Fine Chemical", vol. 35, No. 7, published by CMC publishing Co., Ltd., (2006).

* cited by examiner

*Primary Examiner* — John Pak
(74) *Attorney, Agent, or Firm* — Oblon, Spivak, McClelland, Maier & Neustadt, L.L.P.

(57) ABSTRACT

To provide a pesticidal composition which controls a pest undesirable for cultivation of a useful crop plant or a useful plant. A pesticidal composition comprising the following (component A) and the following (component B) as active ingredients:

(component A): one or more compounds selected from 3-arylphenyl sulfide derivatives represented by the formula [I]:

(component A):

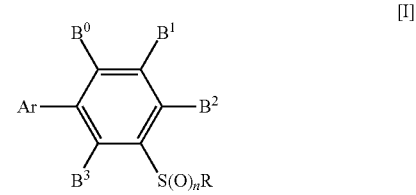

wherein R is a $C_2$-$C_6$ alkyl group which may be substituted, or the like, each of $B^0$, $B^1$, $B^2$ and $B^3$ which are independent of one another, is a hydrogen atom, a halogen atom or a haloalkyl group, n is an integer of from 0 to 2, and Ar is a phenyl group, a pyrazolyl group or a triazolyl group, (component B):
   one or more compounds selected from the group consisting of triazamate, butocarboxim, butoxycarboxim, chromafenozide, halofenozide, cyflumetofen, prallethrin, acetoprole, ethiprole, methamidophos, flonicamid, pyridalyl, flufenerim, flubendiamide, tebufenozide, fenazaquin and cyenopyrafen.

10 Claims, No Drawings

PESTICIDAL COMPOSITION AND METHOD FOR CONTROLLING PEST

TECHNICAL FIELD

The present invention relates to an agriculturally and horticulturally useful pesticidal composition comprising a 3-arylphenyl sulfide derivative represented by the after-mentioned formula [I] as a (component A) and a known pesticide as a (component B), and a method for controlling a pest which comprises applying the respective active ingredients of the (component A) and the (component B) to a pest.

BACKGROUND ART

3-Arylphenyl sulfide derivatives represented by the after-mentioned formula [I] as a (component A) contained in the pesticidal composition of the present invention are disclosed in Patent Documents 1 and 2.

Further, the (component B) contained in the pesticidal composition of the present invention is disclosed in Non-Patent Documents 1 to 3.

A wide variety of pesticides have been put to practical use by research and development over a long period of time, and such pesticides have contributed to improvement in productivity of agricultural and horticultural crop plants. However, even today, development of safer pesticides having more excellent pesticidal activity has been desired.

Further, heretofore, a pesticide to be used against a pest is required to be such an agent that it has a sufficient controlling effect against a wide range of pests at a low dose by application to e.g. a pest, to a useful plant or a useful crop plant, or to the soil in which a useful plant or a useful crop plant grows or to the vicinity thereof, and its effect lasts for a certain period of time.

Patent Document 1: JP-A-2000-198768
Patent Document 2: WO2006/043635
Non-Patent Document 1: Pesticide Manual 13th edition, British Crop Council
Non-Patent Document 2: SHIBUYA INDEX 10th Edition, 11th Edition, published by SHIBUYA INDEX RESEARCH ASSOCIATION
Non-Patent Document 3: Monthly Fine Chemical, vol. 35, No. 7 (2006), published by CMC publishing Co., Ltd.

DISCLOSURE OF THE INVENTION

Object to be Accomplished by the Invention

The object of the present invention is to provide a pesticidal composition comprising a 3-arylphenyl sulfide derivative represented by the following formula [I] to control a pest undesirable for cultivation of a useful crop plant or a useful plant.

Means to Accomplish the Object

The present inventors have conducted extensive studies and as a result, they have found that by use of a (component A) which is a 3-arylphenyl sulfide derivative represented by the following formula [I] and a pesticide represented by the following (component B) in combination, not only a mere additive of the respective pesticidal effects but also a synergistic effect will be obtained.

That is, the present inventors have found that by use of two or more agents in combination, a pesticidal spectrum will be broadened as compared with a pesticidal effect by each agent and in addition, a pesticidal effect will be achieved at an earlier stage and will be retained for a longer time, and a satisfactory effect can be achieved at a lower dose than a dose by a single use of each agent. Further, the use of two or more agents in combination exhibits pesticidal effects against various pests, especially agricultural and horticultural pests such as mites represented by two-spotted spider mite, Kanzawa spider mite and citrus red mite, pest lepidopterans represented by diamondbackmoth, Asiatic rice borer and beat armyworm, pest hemipterans represented by brown rice planthopper, green rice leafhopper and cotton aphid, and pest coleoptera represented by adzuki bean weevil. The present invention has been accomplished on the basis of this discovery.

The present invention provides the following.

(1) A pesticidal composition comprising the following (component A) and the following (component B) as active ingredients:

(component A): one or more compounds selected from 3-arylphenyl sulfide derivatives represented by the formula [I]:

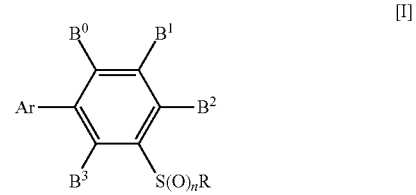

wherein R is a $C_2$-$C_6$ alkyl group (which may be mono-substituted or poly-substituted by a halogen atom or a cyano group), a $C_2$-$C_6$ alkenyl group (which may be mono-substituted or poly-substituted by a halogen atom or a cyano group), a $C_2$-$C_6$ alkynyl group (which may be mono-substituted or poly-substituted by a halogen atom or a cyano group), a $C_3$-$C_6$ cycloalkyl group (which may be mono-substituted or poly-substituted by a halogen atom or a cyano group) or a $C_4$-$C_9$ cycloalkylalkyl group (which may be mono-substituted or poly-substituted by a halogen atom or a cyano group), n is an integer of from 0 to 2, the Ar group is a group represented by the following formula [Ar-1], [Ar-2], [Ar-3] or [Ar-4]:

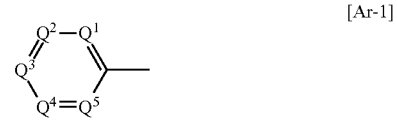

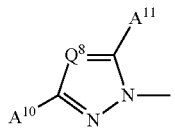
[Ar-4]

in the above formulae, $Q^1$, $Q^2$, $Q^3$, $Q^4$ and $Q^5$ are each independently a nitrogen atom or C-$A^1$, a nitrogen atom or C-$A^2$, a nitrogen atom or C-$A^3$, a nitrogen atom or C-$A^4$, and a nitrogen atom or C-$A^5$, respectively, $Q^6$ is an oxygen atom or a sulfur atom, $Q^7$ is a nitrogen atom or C-$A^7$, $Q^8$ is a nitrogen atom or C-$A^8$, each of $A^1$, $A^{5'}$ $A^7$ and $B^0$ which are independent of one another, is a hydrogen atom, a halogen atom, an amino group, a cyano group, a nitro group, a $C_1$-$C_6$ alkyl group, a $C_1$-$C_4$ haloalkyl group, a $C_1$-$C_6$ alkylthio group (which may be mono-substituted or poly-substituted by a halogen atom) or a $C_1$-$C_6$ alkoxy group, each of $A^2$, $A^3$, $A^4$, $A^6$, $A^9$ $B^1$, $B^2$ and $B^3$ which are independent of one another, is a hydrogen atom, a halogen atom, a cyano group, a nitro group, a $C_1$-$C_6$ alkyl group (which may be mono-substituted or poly-substituted by a halogen atom, a hydroxy group, a cyano group, a $C_2$-$C_7$ alkoxycarbonyl group or a $C_1$-$C_6$ alkoxy group), a $C_2$-$C_6$ alkenyl group (which may be mono-substituted or poly-substituted by a halogen atom or a cyano group), a $C_2$-$C_6$ alkynyl group (which may be mono-substituted or poly-substituted by a halogen atom or a cyano group), a $C_1$-$C_6$ alkoxy group (which may be mono-substituted or poly-substituted by a halogen atom, a cyano group, a $C_2$-$C_5$ alkoxycarbonyl group or a $C_1$-$C_3$ alkoxy group), a $C_1$-$C_6$ alkylthio group (which may be mono-substituted or poly-substituted by a halogen atom or a $C_1$-$C_3$ alkoxy group), a $C_1$-$C_6$ alkylsulfinyl group (which may be mono-substituted or poly-substituted by a halogen atom or a $C_1$-$C_3$ alkoxy group), a $C_1$-$C_6$ alkylsulfonyl group (which may be mono-substituted or poly-substituted by a halogen atom or a $C_1$-$C_3$ alkoxy group), a $C_1$-$C_7$ acyl group, a $C_2$-$C_5$ haloalkylcarbonyl group, a carboxy group, a $C_2$-$C_7$ alkoxycarbonyl group or a —$NR^1R^2$ group [wherein each of $R^1$ and $R^2$ which are independent of each other, is a hydrogen atom, a $C_1$-$C_6$ alkyl group (which may be mono-substituted or poly-substituted by a halogen atom, a cyano group, a hydroxy group, a $C_1$-$C_6$ alkoxy group or a $C_1$-$C_6$ alkylthio group), a $C_2$-$C_6$ alkenyl group (which may be mono-substituted or poly-substituted by a halogen atom or a cyano group), a $C_2$-$C_6$ alkynyl group (which may be mono-substituted or poly-substituted by a halogen atom or a cyano group), a $C_1$-$C_7$ acyl group or a $C_2$-$C_7$ alkoxycarbonyl group, provided that $R^1$ and $R^2$ may form a 5- or 6-membered ring together with the nitrogen atom to which they are bonded], $A^8$ is a hydrogen atom, a halogen atom, a cyano group, a $C_1$-$C_6$ alkyl group (which may be mono-substituted or poly-substituted by a halogen atom or a $C_1$-$C_3$ alkoxy group), a $C_1$-$C_6$ alkoxy group (which may be mono-substituted or poly-substituted by a halogen atom or a $C_1$-$C_3$ alkoxy group), a $C_1$-$C_7$ acyl group, a $C_2$-$C_5$ haloalkylcarbonyl group or a —$NR^1R^2$ group (wherein $R^1$ and $R^2$ are as defined above), $A^{10}$ is a hydrogen atom, a carboxy group, a $C_2$-$C_7$ alkoxycarbonyl group, a halogen atom, a $C_1$-$C_6$ alkyl group (which may be mono-substituted or poly-substituted by a halogen atom, a hydroxy group, a cyano group, a $C_2$-$C_7$ alkoxycarbonyl group or a $C_1$-$C_6$ alkoxy group), a $C_3$-$C_8$ cycloalkyl group (which may be mono-substituted or poly-substituted by an alkyl group, a halogen atom, a cyano group or a $C_1$-$C_6$ alkoxy group), a $C_2$-$C_6$ alkenyl group (which may be mono-substituted or poly-substituted by a halogen atom or a cyano group), a $C_2$-$C_6$ alkynyl group (which may be mono-substituted or poly-substituted by a halogen atom or a cyano group), a $C_1$-$C_6$ alkoxy group (which may be mono-substituted or poly-substituted by a halogen atom, a cyano group, a $C_2$-$C_5$ alkoxycarbonyl group or a $C_1$-$C_3$ alkoxy group), a $C_1$-$C_6$ alkylthio group (which may be mono-substituted or poly-substituted by a halogen atom, a $C_1$-$C_3$ alkoxy group, a $C_3$-$C_8$ cycloalkyl group which may be substituted by a halogen atom, or a cyano group), a $C_1$-$C_6$ alkylsulfinyl group (which may be mono-substituted or poly-substituted by a halogen atom, a $C_1$-$C_3$ alkoxy group, a $C_3$-$C_5$ cycloalkyl group which may be substituted by a halogen atom, or a cyano group), a $C_1$-$C_6$ alkylsulfonyl group (which may be mono-substituted or poly-substituted by a halogen atom, a $C_1$-$C_3$ alkoxy group or a $C_3$-$C_8$ cycloalkyl group which may be substituted by a halogen atom), a $C_2$-$C_6$ alkynylthio group (which may be mono-substituted or poly-substituted by a halogen atom, a $C_1$-$C_3$ alkoxy group or a cyano group), a $C_2$-$C_6$ alkynylsulfinyl group (which may be mono-substituted or poly-substituted by a halogen atom, a $C_1$-$C_3$ alkoxy group or a cyano group), a $C_1$-$C_7$ acyl group or a $C_2$-$C_5$ haloalkylcarbonyl group, $A^{11}$ is a hydrogen atom, a halogen atom, a cyano group, a nitro group, a $C_1$-$C_9$ alkyl group, a $C_1$-$C_4$ haloalkyl group, a $C_1$-$C_6$ alkylthio group (which may be mono-substituted or poly-substituted by a halogen atom), a $C_1$-$C_6$ alkoxy group, a —N=$CR^3R^4$ group, a —N=$C(NR^{4'}R^{5'})NR^4R^5$ group, a —$N(SO_2R^4)R^5$ group, a —$N(OR^5)R^{5'}$ group, a —$C(=O)OR^4$ group, a —$C(=O)NR^4R^5$ group, a —$SO_2NR^4R^5$ group, a —$NR^4R^5$ group, a —$N(COR^4)R^5$ group or a —$N(COOR^4)R^5$ group, $R^3$ is a hydrogen atom, a $C_1$-$C_6$ alkyl group (which may be mono-substituted or poly-substituted by a halogen atom, a hydroxy group, a cyano group, a $C_2$-$C_7$ alkoxycarbonyl group or a $C_1$-$C_6$ alkoxy group), a $C_3$-$C_6$ alkenyl group (which may be mono-substituted or poly-substituted by a halogen atom or a cyano group), a $C_3$-$C_6$ alkynyl group (which may be mono-substituted or poly-substituted by a halogen atom or a cyano group), a $C_3$-$C_6$ cycloalkyl group (which may be mono-substituted or poly-substituted by a halogen atom, a hydroxy group, a cyano group, a $C_2$-$C_7$ alkoxycarbonyl group or a $C_1$-$C_6$ alkoxy group), an arylalkyl group (which may be mono-substituted or poly-substituted by a halogen atom, a cyano group, a $C_1$-$C_6$ alkyl group, a $C_1$-$C_6$ haloalkyl group, a $C_2$-$C_7$ alkoxycarbonyl group or a $C_1$-$C_6$ alkoxy group), a heteroarylalkyl group (which may be mono-substituted or poly-substituted by a halogen atom, a cyano group, a $C_1$-$C_6$ alkyl group, a $C_1$-$C_6$ haloalkyl group, a $C_2$-$C_7$ alkoxycarbonyl group or a $C_1$-$C_6$ alkoxy group), an aryl group (which may be mono-substituted or poly-substituted by a halogen atom, a cyano group, a $C_1$-$C_6$ alkyl group, a $C_1$-$C_6$ haloalkyl group, a $C_2$-$C_7$ alkoxycarbonyl group, a $C_1$-$C_6$ alkoxy group or a hydroxy group), a heteroaryl group (which may be mono-substituted or poly-substituted by a halogen atom, a cyano group, a $C_1$-$C_6$ alkyl group, a $C_1$-$C_6$ haloalkyl group, a $C_2$-$C_7$ alkoxycarbonyl group or a $C_1$-$C_6$ alkoxy group), a $C_1$-$C_6$ alkoxy group, a $C_1$-$C_6$ alkylthio group, an amino group, a $C_1$-$C_6$ monoalkylamino group or a $C_2$-$C_{12}$ dialkylamino group, each of $R^4$ and $R^{4'}$ which are independent of each other, is a hydrogen atom, a $C_1$-$C_6$ alkyl group (which may be mono-substituted or poly-substituted by a halogen atom, a hydroxy group, a cyano group, a $C_2$-$C_7$ alkoxycarbonyl group or a $C_1$-$C_6$ alkoxy group), a $C_3$-$C_6$ alkenyl group (which may be mono-substituted or poly-substituted by a halogen atom or a cyano group), a C₃-C₆ alkynyl group (which may be mono-substituted or poly-substituted by a halogen atom or a cyano group), a C₃-C₆ cycloalkyl group (which may be mono-substituted or poly-substituted by a halogen atom, a hydroxy group, a cyano group, a C₂-C₇ alkoxycarbonyl group or a C₁-C₆ alkoxy group), an amino group, a C₁-C₆ monoalkylamino group, a C₂-C₁₂ dialkylamino group, an arylalkyl group (which may be mono-substituted or poly-substituted by a halogen atom, a cyano group, a C₁-C₆ alkyl group, a C₁-C₆ haloalkyl group, a C₂-C₇ alkoxycarbonyl group or a C₁-C₆ alkoxy group), a heteroarylalkyl group (which may be mono-substituted or poly-substituted by a halogen atom, a cyano group, a C₁-C₆ alkyl group, a C₁-C₆ haloalkyl group, a C₂-C₇ alkoxycarbonyl group or a C₁-C₆ alkoxy group), an aryl group (which may be mono-substituted or poly-substituted by a halogen atom, a cyano group, a C₁-C₆ alkyl group, a C₁-C₆ haloalkyl group, a C₂-C₇ alkoxycarbonyl group or a C₁-C₆ alkoxy group) or a heteroaryl group (which may be mono-substituted or poly-substituted by a halogen atom, a cyano group, a C₁-C₆ alkyl group, a C₁-C₆ haloalkyl group, a C₂-C₇ alkoxycarbonyl group or a C₁-C₆ alkoxy group), and each of R⁵ and R⁵' which are independent of each other, is a hydrogen atom, a C₁-C₆ alkyl group (which may be mono-substituted or poly-substituted by a halogen atom, a hydroxy group, a cyano group, a C₂-C₇ alkoxycarbonyl group or a C₁-C₆ alkoxy group), a C₃-C₆ alkenyl group (which may be mono-substituted or poly-substituted by a halogen atom or a cyano group), a C₃-C₆ alkynyl group (which may be mono-substituted or poly-substituted by a halogen atom or a cyano group) or a C₃-C₆ cycloalkyl group (which may be mono-substituted or poly-substituted by a halogen atom, a hydroxy group, a cyano group, a C₂-C₇ alkoxycarbonyl group or a C₁-C₆ alkoxy group), provided that in a case where the Ar group is the formula [Ar-1] or [Ar-2], at most 2 of Q¹ to Q⁵ can be a nitrogen atom, in a case where the Ar group is the formula [Ar-1] and only Q⁵ is a nitrogen atom, A¹ is a hydrogen atom, in a case where the Ar group is the formula [Ar-1] and Q¹, Q², Q³, Q⁴ and Q⁵ are C-A¹, C-A², C-A³, C-A⁴ and C-A⁵, respectively, A², A³, A⁴ and B² are not simultaneously a hydrogen atom, in a case where all of A¹ to A⁵ are a hydrogen atom, a compound wherein B² is a methyl group and R is an isopropyl group is excluded, and in a case where the Ar group is the formula [Ar-4] and Q⁸ is C-A⁵, R is a C₂-C₆ alkyl group (which may be mono-substituted or poly-substituted by a halogen atom), a C₃-C₆ cycloalkyl group (which may be mono-substituted or poly-substituted by a halogen atom) or a C₄-C₉ cycloalkylalkyl group (which may be mono-substituted or poly-substituted by a halogen atom), (component B):
one or more compounds or components selected from the group consisting of acylurea compounds such as bistrifluoron, novaluron and noviflumuron, carbamate compounds such as xylylcarb, thiofanox, triazamate, trimethacarb, butocarboxim, formetanate and methiocarb, diacylhydrazine compounds such as chromafenozide, halofenozide and methoxyfenozide, nereistoxin compounds such as thiosultap-sodium, pyrethroid compounds such as imiprothrin, esfenvalerate, empenthrin, cyphenothrin, cyflumetofen, transfluthrin, halfenprox, bioallethrin, bioresmethrin, prallethrin, flumethrin, methothrin, RU-15525 and ZXI-8901, phenyl pyrazole compounds such as acetoprole and ethiprole, organophosphorus compounds such as azamethiphos, isocarbophos, imicyafos, omethoate, cadusafos, coumaphos, chlormephos, dicrotophos, sulfotep, tebupirimfos, demeton-S-methyl, temephos, terbufos, triazophos, parathion, famphur, flupyrazofos, propetamphos, heptenophos, phoxim, phosphamidon, phorate, mecarbam, methamidophos and mevinphos, juvenile hormone-like compounds such as hydroprene and kinoprene, and flonicamid, pyridalyl, flufenerim, flubendiamide, tebufenozide, metaflumizone, spirotetramat, CL900167, spiromesifen, cyflumetofen, dienochlor, fenazaquin and cyenopyrafen.

(2) The pesticidal composition according to the above (1), wherein in the compound represented by the formula [I], the Ar group is the formula [Ar-4]:

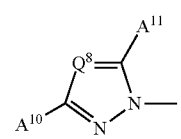

[Ar-4]

Q⁸ is a nitrogen atom, and R is a C₂-C₆ alkyl group (which may be mono-substituted or poly-substituted by a halogen atom) or a C₄-C₉ cycloalkylalkyl group (which may be mono-substituted or poly-substituted by a halogen atom).

(3) The pesticidal composition according to the above (1), wherein in the compound represented by the formula [I], the Ar group is the formula [Ar-4]:

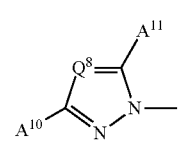

[Ar-4]

Q⁸ is a nitrogen atom, R is a trifluoroethyl group, n is 0 or 1, A¹⁰ is a C₁-C₆ alkyl group (which may be mono-substituted or poly-substituted by a halogen atom or a cyano group), a C₁-C₆ alkylthio group (which may be mono-substituted or poly-substituted by a halogen atom) or a C₁-C₆ alkylsulfinyl group (which may be mono-substituted or poly-substituted by a halogen atom or a C₁-C₃ alkoxy group), A¹¹ is a hydrogen atom, a group —NR⁴R⁵ or a group —N(COR⁴)R⁵, each of R⁴ and R⁵ which are independent of each other, is a hydrogen atom, a C₁-C₆ alkylamino group, a C₁-C₆ alkyl group (which may be mono-substituted or poly-substituted by a halogen atom or a cyano group) or a C₃-C₆ alkynyl group (which may be mono-substituted or poly-substituted by a halogen atom or a cyano group), B⁰ is a hydrogen atom, a halogen atom or a methyl group, and B² is a cyano group or a C₁-C₆ alkyl group (which may be mono-substituted or poly-substituted by a halogen atom).

(4) The pesticidal composition according to the above (1), wherein in the compound represented by the formula [I], the Ar group is the formula [Ar-4]:

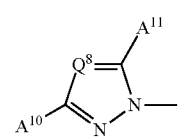

[Ar-4]

$Q^8$ is a nitrogen atom, R is a trifluoroethyl group, n is 0 or 1, $A^{10}$ is a $C_1$-$C_6$ alkyl group (which may be mono-substituted or poly-substituted by a halogen atom or a cyano group), a $C_1$-$C_6$ alkylthio group (which may be mono-substituted or poly-substituted by a halogen atom) or a $C_1$-$C_6$ alkylsulfinyl group (which may be mono-substituted or poly-substituted by a halogen atom or a $C_1$-$C_3$ alkoxy group), $A^{11}$ is a group —$NH_2$, $B^0$ is a halogen atom or a methyl group, and $B^2$ is a cyano group or a $C_1$-$C_6$ alkyl group (which may be mono-substituted or poly-substituted by a halogen atom).

(5) A method for controlling a pest, which comprises directly spraying the pesticidal composition as defined in any one of the above (1) to (4) to the surface of a plant or to the pest.

(6) A method for controlling a pest, which comprises applying the pesticidal composition as defined in any one of the above (1) to (4) directly to the soil or directly to seeds, seed tubers or bulbs or to the vicinity thereof.

(7) A method for controlling a pest, which comprises mixing the (component A) and the (component B) as defined in any one of the above (1) to (4) and applying them in the form of a mixed solution to a nursery soil by irrigation or spraying them in the form of a mixed granule to a nursery soil, between sowing of seeds and planting of seedlings of a crop plant cultivated by a method of planting seedlings.

(8) A method for controlling a pest, which comprises cultivating seedlings by using a nursery soil containing the (component A) and the (component B) as defined in any one of the above (1) to (4) between sowing of seeds and planting of seedlings of a crop plant cultivated by a method of planting seedlings.

(9) A method for controlling a pest, which comprises applying the (component A) and the (component B) as defined in any one of the above (1) to (4) to the soil of a field by irrigation, spraying of a granule, soil incorporation, row application, planting furrow application, planting hole application, planting hole soil incorporation, plant root zone application or plant root zone soil incorporation, at the time of planting seedlings or during growth of a crop plant cultivated by a method of planting seedlings.

(10) A method for controlling a pest, which comprises applying the (component A) and the (component B) as defined in any one of the above (1) to (4) directly to seeds, seed tubers or bulbs or to the vicinity thereof of a crop plant cultivated by directly sowing seeds, seed tubers or bulbs to a field, by impregnation, by dust coating, by covering, by coating or by enclosing the seeds, the seed tubers or the bulbs with a tape containing such compounds.

(11) A method for controlling a pest, which comprises applying the (component A) and the (component B) as defined in any one of the above (1) to (4) to a soil of a field by irrigation, spraying of a granule, soil incorporation, row application, sowing furrow application, plant root zone application or plant root zone soil incorporation, at the time of sowing or during growth of a crop plant cultivated by directly sowing seeds, seed tubers or bulbs to a field.

(12) A method for controlling a pest, which comprises separately applying the (component A) and the (component B) as defined in any one of the above (1) to (4) with an interval.

Effects of the Invention

The pesticidal compositions of the present invention exhibit excellent pesticidal effects against a wide range of pests including pest hemiptera, pest lepidoptera, pest coleoptera, pest diptera, pest hymenoptera, pest orthoptera, pest isoptera, pest thysanoptera, mites and plant-parastic nematodes, and they are also capable of controlling pests which have acquired resistance.

BEST MODE FOR CARRYING OUT THE INVENTION

The terms used in this specification will be defined below.

The halogen atom represents a fluorine atom, a chlorine atom, a bromine atom or an iodine atom.

The $C_1$-$C_6$ alkyl group means, unless otherwise specified, a linear or branched alkyl group having from 1 to 6 carbon atoms, such as a methyl group, an ethyl group, a n-propyl group, an isopropyl group, a n-butyl group, an isobutyl group, a sec-butyl group, a tert-butyl group, a pentyl group or a hexyl group.

The $C_3$-$C_6$ cycloalkyl group means a cycloalkyl group having from 3 to 6 carbon atoms, such as a cyclopropyl group, a cyclopentyl group or a cyclohexyl group.

The $C_4$-$C_9$ cycloalkylalkyl group means an alkyl group having from 1 to 3 carbon atoms substituted by a cycloalkyl group having from 3 to 6 carbon atoms, such as a cyclopropylmethyl group, a cyclopentylmethyl group or a cyclohexylmethyl group.

The $C_2$-$C_6$ alkenyl group means a linear or branched alkenyl group having from 2 to 6 carbon atoms, such as an ethenyl group or a 2-propenyl group.

The $C_2$-$C_6$ alkynyl group means a linear or branched alkynyl group having from 2 to 6 carbon atoms, such as an ethynyl group or a 2-propynyl group.

The $C_1$-$C_4$ haloalkyl group means, unless otherwise specified, a linear or branched alkyl group having from 1 to 4 carbon atoms substituted by from 1 to 9 identical or different halogen atoms, such as a chloromethyl group, a trifluoromethyl group or a tetrafluoroethyl group.

The $C_1$-$C_3$ alkoxy group means a ($C_1$-$C_3$ alkyl)-O— group wherein the alkyl moiety is methyl, ethyl, propyl or isopropyl, such as a methoxy group, an ethoxy group, a propoxy group or an isopropoxy group.

The $C_1$-$C_6$ alkoxy group means a ($C_1$-$C_6$ alkyl)-O— group wherein the alkyl moiety is a linear or branched alkyl group having from 1 to 6 carbon atoms, such as the above-exemplified groups, or a butoxy group, a pentyloxy group or a hexyloxy group.

The $C_1$-$C_6$ alkylthio group means a ($C_1$-$C_6$ alkyl)-S— group wherein the alkyl moiety is as defined above, such as a methylthio group, an ethylthio group, a propylthio group, a butylthio group or a hexylthio group.

The $C_1$-$C_6$ alkylsulfinyl group means a ($C_1$-$C_6$ alkyl)-SO— group wherein the alkyl moiety is as defined above, such as a methylsulfinyl group, an ethylsulfinyl group, a propylsulfinyl group, a butylsulfinyl group or a hexylsulfinyl group.

The $C_1$-$C_6$ alkylsulfonyl group means a ($C_1$-$C_6$ alkyl)(alkyl)-$SO_2$— group wherein the alkyl moiety is as defined above, such as a methylsulfonyl group, an ethylsulfonyl group, a propylsulfonyl group, a butylsulfonyl group or a hexylsulfonyl group.

The $C_1$-$C_7$ acyl group means a formyl group or a ($C_1$-$C_6$ alkyl)-CO— group wherein the alkyl moiety is as defined above, such as an acetyl group or a propionyl group.

The $C_2$-$C_5$ alkoxycarbonyl group means a ($C_1$-$C_4$ alkoxy)-C(=O)— group wherein the alkyl in the alkoxy moiety is linear or branched and has from 1 to 4 carbon atoms, such as a methoxycarbonyl group, an ethoxycarbonyl group or a butoxycarbonyl group.

The $C_2$-$C_7$ alkoxycarbonyl group means a ($C_1$-$C_6$ alkoxy)-C(=O)— group wherein the alkyl in the alkoxy moiety is linear or branched and has from 1 to 6 carbon atoms, such as the above-exemplified group or a pentyloxycarbonyl group or a hexyloxycarbonyl group.

The $C_2$-$C_5$ haloalkoxycarbonyl group means a ($C_1$-$C_4$ haloalkoxy)-C(=O)— group wherein the haloalkyl is as defined above, such as a trifluoroacetyl group or a 2,2,2-trifluoroethylcarbonyl group.

Representative specific examples of the compound represented by the formula [I] are disclosed in JP-A-2000-198768 or WO99/55668. Further, among the representative specific examples, preferred specific examples will be given in Tables 1 to 14.

The compound numbers will be referred to in the subsequent description.

The symbols in the Tables in this specification denote the following respective corresponding groups.

| | |
|---|---|
| Me: | methyl group, |
| Pr: | n-propyl group, |
| Pr-c: | cyclopropyl group, |
| Bu-i: | isobutyl group, |
| Bu-t: | tert-butyl group, |
| Pen: | n-pentyl group, |
| Pen-c: | cyclopentyl group, |
| Et: | ethyl group, |
| Pr-i: | isopropyl group, |
| Bu: | n-butyl group, |
| Bu-s: | sec-butyl group, |
| Bu-c: | cyclobutyl group, |
| Pen-i: | isopentyl group, |
| Hex-c: | cyclohexyl group. |

TABLE 1

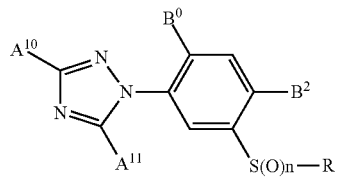

| Compound No. | $A^{10}$ | $A^{11}$ | $B^0$ | $B^2$ | R | n | Melting point (° C.) or refractive index ($n_D^{20}$) |
|---|---|---|---|---|---|---|---|
| 1 | $CF_3$ | $NH_2$ | F | Me | $CH_2CF_3$ | 0 | 171-173 |
| 2 | $CF_3$ | $NH_2$ | F | Me | $CH_2CF_3$ | 1 | 236-238 |
| 3 | $CF_3$ | $NH_2$ | F | Me | $CH_2Pr$-c | 0 | 179-181 |
| 4 | $CF_3$ | $NH_2$ | F | Me | $CH_2Pr$-c | 1 | 207-209 |
| 5 | $CF_3$ | $NHCOCF_3$ | F | Me | $CH_2CF_3$ | 0 | 122-125 |
| 6 | $CF_3$ | $NHCOCF_3$ | F | Me | $CH_2CF_3$ | 1 | 233-237 |
| 7 | $CF_3$ | $NH_2$ | Cl | Me | $CH_2CF_3$ | 0 | 193-194 |
| 8 | $CF_3$ | $NH_2$ | Cl | Me | $CH_2CF_3$ | 1 | 235-237 |
| 9 | $CF_3$ | $NH_2$ | Me | Cl | $CH_2CF_3$ | 0 | 183-185 |
| 10 | $CF_3$ | $NH_2$ | Me | Cl | $CH_2CF_3$ | 1 | 249-251 |
| 11 | $NO_2$ | H | H | $CHF_2$ | $CH_2CF_3$ | 0 | 74-76 |
| 12 | $NO_2$ | H | H | $CHF_2$ | $CH_2CF_3$ | 1 | 155-156 |
| 13 | $NO_2$ | H | H | CN | $CH_2CF_3$ | 0 | |
| 14 | $NO_2$ | H | H | CN | $CH_2CF_3$ | 1 | |
| 15 | SMe | $NH_2$ | F | Me | $CH_2CF_3$ | 0 | 130-131 |
| 16 | SMe | $NH_2$ | F | Me | $CH_2CF_3$ | 1 | |
| 17 | SOMe | $NH_2$ | F | Me | $CH_2CF_3$ | 0 | 158-160 |
| 18 | SOMe | $NH_2$ | F | Me | $CH_2CF_3$ | 1 | 181-183 |
| 19 | $SO_2Me$ | $NH_2$ | F | Me | $CH_2CF_3$ | 0 | |
| 20 | $SO_2Me$ | $NH_2$ | F | Me | $CH_2CF_3$ | 1 | 218-219 |
| 21 | SEt | $NH_2$ | F | Me | $CH_2CF_3$ | 0 | 87-89 |
| 22 | SEt | $NH_2$ | F | Me | $CH_2CF_3$ | 1 | |
| 23 | SOEt | $NH_2$ | F | Me | $CH_2CF_3$ | 0 | 156-157 |
| 24 | SOEt | $NH_2$ | F | Me | $CH_2CF_3$ | 1 | 201-203 |

TABLE 1-continued

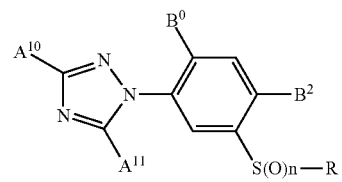

| Compound No. | $A^{10}$ | $A^{11}$ | $B^0$ | $B^2$ | R | n | Melting point (° C.) or refractive index ($n_D^{20}$) |
|---|---|---|---|---|---|---|---|
| 25 | $SO_2Et$ | $NH_2$ | F | Me | $CH_2CF_3$ | 0 | |
| 26 | $SO_2Et$ | $NH_2$ | F | Me | $CH_2CF_3$ | 1 | 204-205 |
| 27 | $SCHF_2$ | $NH_2$ | F | Me | $CH_2CF_3$ | 0 | 107-109 |
| 28 | $SCHF_2$ | $NH_2$ | F | Me | $CH_2CF_3$ | 1 | 189-191 |
| 29 | $S(O)CHF_2$ | $NH_2$ | F | Me | $CH_2CF_3$ | 0 | |
| 30 | $S(O)CHF_2$ | $NH_2$ | F | Me | $CH_2CF_3$ | 1 | 199-202 |
| 31 | $SCF_3$ | $NH_2$ | F | Me | $CH_2CF_3$ | 0 | 111-113 |
| 32 | $SCF_3$ | $NH_2$ | F | Me | $CH_2CF_3$ | 1 | 205-207 |
| 33 | CN | H | F | Me | $CH_2CF_3$ | 0 | |
| 34 | CN | H | F | Me | $CH_2CF_3$ | 1 | |
| 35 | CN | $NH_2$ | F | Me | $CH_2CF_3$ | 0 | 130-131 |

TABLE 2

| Compound No. | $A^{10}$ | $A^{11}$ | $B^0$ | $B^2$ | R | n | Melting point (° C.) or refractive index ($n_D^{20}$) |
|---|---|---|---|---|---|---|---|
| 36 | CN | $NH_2$ | F | Me | $CH_2CF_3$ | 1 | 184-186 |
| 37 | $CF_3$ | NHMe | H | Me | $CH_2CF_3$ | 0 | 120-122 |
| 38 | $CF_3$ | NHMe | H | Me | $CH_2CF_3$ | 1 | 196-198 |
| 39 | $CF_3$ | NHMe | F | Me | $CH_2CF_3$ | 0 | 150-151 |
| 40 | $CF_3$ | NHMe | F | Me | $CH_2CF_3$ | 1 | 147-148 |
| 41 | $CF_3$ | $N(Me)_2$ | H | Me | $CH_2CF_3$ | 0 | |
| 42 | $CF_3$ | $N(Me)_2$ | H | Me | $CH_2CF_3$ | 1 | |
| 43 | $CF_3$ | $N(Me)_2$ | F | Me | $CH_2CF_3$ | 0 | 111-114 |
| 44 | $CF_3$ | $N(Me)_2$ | F | Me | $CH_2CF_3$ | 1 | |
| 45 | $CF_3$ | $NHSO_2Me$ | H | Me | $CH_2CF_3$ | 0 | |
| 46 | $CF_3$ | $NHSO_2Me$ | H | Me | $CH_2CF_3$ | 1 | |
| 47 | $CF_3$ | $NHSO_2Me$ | F | Me | $CH_2CF_3$ | 0 | |
| 48 | $CF_3$ | $NHSO_2Me$ | F | Me | $CH_2CF_3$ | 1 | |
| 49 | Et | $NH_2$ | F | Me | $CH_2CF_3$ | 0 | Measurement impossble |
| 50 | Et | $NH_2$ | F | Me | $CH_2CF_3$ | 1 | 195-197 |
| 51 | Cl | $NH_2$ | F | Me | $CH_2CF_3$ | 0 | |
| 52 | Cl | $NH_2$ | F | Me | $CH_2CF_3$ | 1 | |
| 53 | Br | $NH_2$ | F | Me | $CH_2CF_3$ | 0 | |
| 54 | Br | $NH_2$ | F | Me | $CH_2CF_3$ | 1 | |
| 55 | $CF_3$ | $NH_2$ | Me | Me | $CH_2CF_3$ | 0 | 176-178 |
| 56 | $CF_3$ | $NH_2$ | Me | Me | $CH_2CF_3$ | 1 | 256-257 |
| 57 | $CF_3$ | pyrrolidinyl | F | Me | $CH_2CF_3$ | 0 | |
| 58 | $CF_3$ | pyrrolidinyl | F | Me | $CH_2CF_3$ | 1 | |
| 59 | $CF_3$ | NHEt | F | Me | $CH_2CF_3$ | 0 | 1.4988 |
| 60 | $CF_3$ | NHEt | F | Me | $CH_2CF_3$ | 1 | 149-152 |
| 61 | $CF_3$ | NHPr | F | Me | $CH_2CF_3$ | 0 | |
| 62 | $CF_3$ | NHPr | F | Me | $CH_2CF_3$ | 1 | |
| 63 | $CF_3$ | $NHCH_2CH=CH_2$ | F | Me | $CH_2CF_3$ | 0 | |
| 64 | $CF_3$ | $NHCH_2CH=CH_2$ | F | Me | $CH_2CF_3$ | 1 | |
| 65 | $CF_3$ | $NHCH_2C≡CH$ | F | Me | $CH_2CF_3$ | 0 | 76-78 |
| 66 | $CF_3$ | $NHCH_2C≡CH$ | F | Me | $CH_2CF_3$ | 1 | 152-154 |

TABLE 2-continued

| Compound No. | $A^{10}$ | $A^{11}$ | $B^0$ | $B^2$ | R | n | Melting point (°C.) or refractive index ($n_p^{20}$) |
|---|---|---|---|---|---|---|---|
| 67 | $CF_3$ | $NHCH_2Ph$-4-Cl | F | Me | $CH_2CF_3$ | 0 | |
| 68 | $CF_3$ | $NHCH_2Ph$-4-Cl | F | Me | $CH_2CF_3$ | 1 | |
| 69 | $CF_3$ | $NHCH_2$-3-Py-6-Cl | F | Me | $CH_2CF_3$ | 0 | |
| 70 | $CF_3$ | $NHCH_2$-3-Py-6-Cl | F | Me | $CH_2CF_3$ | 1 | |
| 71 | $CF_3$ | NH—Ph-2,6-$Cl_2$-4-$CF_3$ | F | Me | $CH_2CF_3$ | 0 | |
| 72 | $CF_3$ | NH—Ph-2,6-$Cl_2$-4-$CF_3$ | F | Me | $CH_2CF_3$ | 1 | |

TABLE 3

| Compound No. | $A^{10}$ | $A^{11}$ | $B^0$ | $B^2$ | R | n | Melting point (°C.) or refractive index ($n_p^{20}$) |
|---|---|---|---|---|---|---|---|
| 73 | $CF_3$ | NH-2-Py-3-Cl-5-$CF_3$ | F | Me | $CH_2CF_3$ | 0 | |
| 74 | $CF_3$ | NH-2-Py-3-Cl-6-$CF_3$ | F | Me | $CH_2CF_3$ | 1 | |
| 75 | $CF_3$ | NHCOMe | F | Me | $CH_2CF_3$ | 0 | 133-135 |
| 76 | $CF_3$ | NHCOMe | F | Me | $CH_2CF_3$ | 1 | 159-161 |
| 77 | $CF_3$ | $NHCOCH_2OMe$ | F | Me | $CH_2CF_3$ | 0 | |
| 78 | $CF_3$ | $NHCOCH_2OMe$ | F | Me | $CH_2CF_3$ | 1 | |
| 79 | $CF_3$ | NHCOOMe | F | Me | $CH_2CF_3$ | 0 | 131-133 |
| 80 | $CF_3$ | NHCOOMe | F | Me | $CH_2CF_3$ | 1 | 167-169 |
| 81 | $CF_3$ | $NHCONH_2$ | F | Me | $CH_2CF_3$ | 0 | |
| 82 | $CF_3$ | $NHCONH_2$ | F | Me | $CH_2CF_3$ | 1 | |
| 83 | $CF_3$ | $NHCONMe_2$ | F | Me | $CH_2CF_3$ | 0 | 142-144 |
| 84 | $CF_3$ | $NHCONMe_2$ | F | Me | $CH_2CF_3$ | 1 | 100-103 |
| 85 | $CF_3$ | $NHSO_2NMe_2$ | F | Me | $CH_2CF_3$ | 0 | |
| 86 | $CF_3$ | $NHSO_2NMe_2$ | F | Me | $CH_2CF_3$ | 1 | |
| 87 | $CF_3$ | $NHSO_2CF_3$ | F | Me | $CH_2CF_3$ | 0 | |
| 88 | $CF_3$ | $NHSO_2CF_3$ | F | Me | $CH_2CF_3$ | 1 | |
| 89 | $CF_3$ | N=CH—Ph-4-OH-3-OMe | F | Me | $CH_2CF_3$ | 0 | |
| 90 | $CF_3$ | N=CH—Ph-4-OH-3-OMe | F | Me | $CH_2CF_3$ | 1 | |
| 91 | $CF_3$ | $N=CMe_2$ | F | Me | $CH_2CF_3$ | 0 | |
| 92 | $CF_3$ | $N=CMe_2$ | F | Me | $CH_2CF_3$ | 1 | |
| 93 | $CF_3$ | $N=C(NH_2)_2$ | F | Me | $CH_2CF_3$ | 0 | |
| 94 | $CF_3$ | $N=C(NH_2)_2$ | F | Me | $CH_2CF_3$ | 1 | |
| 95 | $CF_3$ | NH=C(NH)(NH)-cyclic | F | Me | $CH_2CF_3$ | 0 | |
| 96 | $CF_3$ | NH=C(NH)(NH)-cyclic | F | Me | $CH_2CF_3$ | 1 | |
| 97 | $CF_3$ | NHMe | Cl | Me | $CH_2CF_3$ | 0 | 116-118 |
| 98 | $CF_3$ | NHMe | Cl | Me | $CH_2CF_3$ | 1 | 181-182 |
| 99 | $SCF_3$ | $NHCOCF_3$ | F | Me | $CH_2CF_3$ | 0 | 180-181 |
| 100 | $SCF_3$ | $NHCOCF_3$ | F | Me | $CH_2CF_3$ | 1 | |
| 101 | $SC_2F_5$ | NHMe | F | Me | $CH_2CF_3$ | 0 | 1.5028 |
| 102 | $SC_2F_5$ | NHMe | F | Me | $CH_2CF_3$ | 1 | 141-143 |
| 103 | $C(Me)_2CN$ | $NH_2$ | F | Me | $CH_2CF_3$ | 0 | 156-157 |
| 104 | $C(Me)_2CN$ | $NH_2$ | F | Me | $CH_2CF_3$ | 1 | 194-195 |
| 105 | Me | $NH_2$ | F | Me | $CH_2CF_3$ | 0 | 171-172 |
| 106 | Me | $NH_2$ | F | Me | $CH_2CF_3$ | 1 | 180-182 |
| 106 | $CH_2Bu$-t | $NH_2$ | F | Me | $CH_2CF_3$ | 0 | 138-139 |
| 107 | $CH_2Bu$-t | $NH_2$ | F | Me | $CH_2CF_3$ | 1 | 186-186 |
| 108 | $CF_3$ | NHCOMe | Cl | Me | $CH_2CF_3$ | 0 | 157-159 |
| 109 | $CF_3$ | NHCOMe | Cl | Me | $CH_2CF_3$ | 1 | |

TABLE 4

| Compound No. | $A^{10}$ | $A^{11}$ | $B^0$ | $B^2$ | R | n | Melting point (°C.) or refractive index ($n_p^{20}$) |
|---|---|---|---|---|---|---|---|
| 110 | Pr-i | $NH_2$ | F | Me | $CH_2CF_3$ | 0 | 149-151 |
| 111 | Pr-i | $NH_2$ | F | Me | $CH_2CF_3$ | 1 | 146-148 |
| 112 | Bu-t | NHCOMe | F | Me | $CH_2CF_3$ | 0 | 170-172 |
| 113 | Bu-t | NHCOMe | F | Me | $CH_2CF_3$ | 1 | 156-157 |
| 114 | Bu-t | NHMe | F | Me | $CH_2CF_3$ | 0 | 125-128 |
| 115 | Bu-t | NHMe | F | Me | $CH_2CF_3$ | 1 | 147-150 |
| 116 | Et | $NH_2$ | F | Me | $CH_2CF_3$ | 0 | 169-172 |
| 117 | Et | $NH_2$ | F | Me | $CH_2CF_3$ | 1 | 199-200 |
| 118 | $C(Me)_2Et$ | $NH_2$ | F | Me | $CH_2CF_3$ | 0 | 140-142 |
| 119 | $C(Me)_2Et$ | $NH_2$ | F | Me | $CH_2CF_3$ | 1 | 154-156 |
| 120 | $CF_3$ | $NH_2$ | H | CN | $CH_2CF_3$ | 0 | 163-165 |
| 121 | $CF_3$ | $NH_2$ | H | CN | $CH_2CF_3$ | 1 | 204-206 |
| 122 | $CF_3$ | $NH_2$ | H | $CHF_2$ | $CH_2CF_3$ | 0 | |
| 123 | $CF_3$ | $NH_2$ | H | $CHF_2$ | $CH_2CF_3$ | 1 | 205-206 |
| 124 | $CF_3$ | $NH_2$ | H | Me | $CH_2CF_3$ | 0 | 135-137 |
| 125 | $CF_3$ | $NH_2$ | H | Me | $CH_2CF_3$ | 1 | 207-208 |
| 126 | $CF_3$ | $NH_2$ | H | Cl | $CH_2CF_3$ | 0 | 147-149 |
| 127 | $CF_3$ | $NH_2$ | H | Cl | $CH_2CF_3$ | 1 | 164-167 |
| 128 | $CF_3$ | $N(Et)_2$ | F | Me | $CH_2CF_3$ | 0 | 1.4811 |
| 129 | $CF_3$ | $N(Et)_2$ | F | Me | $CH_2CF_3$ | 1 | |
| 130 | $SCH_2CF_3$ | $NH_2$ | F | Me | $CH_2CF_3$ | 0 | 109-110 |
| 131 | $SCH_2CF_3$ | $NH_2$ | F | Me | $CH_2CF_3$ | 1 | 152-154 |
| 132 | $S(O)CH_2CF_3$ | $NH_2$ | F | Me | $CH_2CF_3$ | 0 | |
| 133 | $S(O)CH_2CF_3$ | $NH_2$ | F | Me | $CH_2CF_3$ | 1 | 195-197 |
| 134 | SPr | $NH_2$ | F | Me | $CH_2CF_3$ | 0 | 81-84 |
| 135 | SPr | $NH_2$ | F | Me | $CH_2CF_3$ | 1 | |
| 136 | S(O)Pr | $NH_2$ | F | Me | $CH_2CF_3$ | 0 | 140-141 |
| 137 | S(O)Pr | $NH_2$ | F | Me | $CH_2CF_3$ | 1 | 196-197 |
| 138 | $S(O)_2Pr$ | $NH_2$ | F | Me | $CH_2CF_3$ | 0 | |

TABLE 4-continued

| Compound No. | $A^{10}$ | $A^{11}$ | $B^0$ | $B^2$ | R | n | Melting point (°C.) or refractive index ($n_p^{20}$) |
|---|---|---|---|---|---|---|---|
| 139 | $S(O)_2Pr$ | $NH_2$ | F | Me | $CH_2CF_3$ | 1 | 198-199 |
| 140 | $SCH_2CN$ | $NH_2$ | F | Me | $CH_2CF_3$ | 0 | 110-111 |
| 141 | $SCH_2CN$ | $NH_2$ | F | Me | $CH_2CF_3$ | 1 | 138-140 |
| 142 | $S(O)CH_2CN$ | $NH_2$ | F | Me | $CH_2CF_3$ | 0 | |
| 143 | $S(O)CH_2CN$ | $NH_2$ | F | Me | $CH_2CF_3$ | 1 | 193-195 |
| 144 | Bu-t | $NH_2$ | F | Me | $CH_2CF_3$ | 0 | 49-51 |
| 145 | Bu-t | $NH_2$ | F | Me | $CH_2CF_3$ | 1 | 102-104 |
| 146 | $CF_3$ | NHMe | Me | Me | $CH_2CF_3$ | 0 | 91-93 |
| 147 | $CF_3$ | NHMe | Me | Me | $CH_2CF_3$ | 1 | 203-205 |
| 148 | $SCH_2C{\equiv}CH$ | $NH_2$ | F | Me | $CH_2CF_3$ | 0 | 69-71 |
| 149 | $SCH_2C{\equiv}CH$ | $NH_2$ | F | Me | $CH_2CF_3$ | 1 | |
| 150 | $S(O)CH_2C{\equiv}CH$ | $NH_2$ | F | Me | $CH_2CF_3$ | 0 | 127-128 |
| 151 | $S(O)CH_2C{\equiv}CH$ | $NH_2$ | F | Me | $CH_2CF_3$ | 1 | 92-95 |
| 152 | $CF_3$ | $NHCOCF_3$ | H | Me | $CH_2CF_3$ | 0 | |
| 153 | $CF_3$ | $NHCOCF_3$ | H | Me | $CH_2CF_3$ | 1 | 147-149 |

TABLE 5

| Compound No. | $A^{10}$ | $A^{11}$ | $B^0$ | $B^2$ | R | n | Melting point (°C.) or refractive index ($n_p^{20}$) |
|---|---|---|---|---|---|---|---|
| 154 | $SCH_2CF_3$ | NHCOMe | F | Me | $CH_2CF_3$ | 0 | 147-149 |
| 155 | $SCH_2CF_3$ | NHCOMe | F | Me | $CH_2CF_3$ | 1 | 163-166 |
| 156 | $S(O)CH_2CF_3$ | NHCOMe | F | Me | $CH_2CF_3$ | 0 | |
| 157 | $S(O)CH_2CF_3$ | NHCOMe | F | Me | $CH_2CF_3$ | 1 | 89-92 |
| 158 | $SCH_2CF_3$ | N(Me)COMe | F | Me | $CH_2CF_3$ | 0 | 1.5175 |
| 159 | $SCH_2CF_3$ | N(Me)COMe | F | Me | $CH_2CF_3$ | 1 | |
| 160 | $SCH_2CF_3$ | NHMe | F | Me | $CH_2CF_3$ | 0 | 91-93 |
| 161 | $SCH_2CF_3$ | NHMe | F | Me | $CH_2CF_3$ | 1 | 50-53 |
| 162 | $CF_3$ | $NHNH_2$ | F | Me | $CH_2CF_3$ | 0 | 113-115 |
| 163 | $CF_3$ | $NHNH_2$ | F | Me | $CH_2CF_3$ | 1 | 195-197 |
| 164 | $CF_3$ | $NHCH_2CN$ | F | Me | $CH_2CF_3$ | 0 | 112-114 |
| 165 | $CF_3$ | $NHCH_2CN$ | F | Me | $CH_2CF_3$ | 1 | 130-132 |
| 166 | $CF_3$ | NHPr-i | F | Me | $CH_2CF_3$ | 0 | |
| 167 | $CF_3$ | NHPr-i | F | Me | $CH_2CF_3$ | 1 | 93-95 |
| 168 | $CF_3$ | NHCONHMe | F | Me | $CH_2CF_3$ | 0 | 132-133 |
| 169 | $CF_3$ | NHCONHMe | F | Me | $CH_2CF_3$ | 1 | 107-109 |
| 170 | $CF_3$ | $N(Me)NH_2$ | F | Me | $CH_2CF_3$ | 0 | 53-55 |
| 171 | $CF_3$ | $N(Me)NH_2$ | F | Me | $CH_2CF_3$ | 1 | 138-139 |
| 172 | $SC_3F_7$ | $NH_2$ | F | Me | $CH_2CF_3$ | 0 | 102-104 |
| 173 | $SC_3F_7$ | $NH_2$ | F | Me | $CH_2CF_3$ | 1 | 208-211 |
| 174 | $C_3F_7$ | $NH_2$ | F | Me | $CH_2CF_3$ | 0 | 97-98 |
| 175 | $C_3F_7$ | $NH_2$ | F | Me | $CH_2CF_3$ | 1 | 193-195 |
| 176 | $SC_2F_5$ | $NH_2$ | F | Me | $CH_2CF_3$ | 0 | 113-115 |
| 177 | $SC_2F_5$ | $NH_2$ | F | Me | $CH_2CF_3$ | 1 | 209-211 |
| 178 | 1-methylcyclopropyl | $NH_2$ | F | Me | $CH_2CF_3$ | 0 | 178-179 |
| 179 | 1-methylcyclopropyl | $NH_2$ | F | Me | $CH_2CF_3$ | 1 | 206-208 |
| 180 | 1-methylcyclohexyl | $NH_2$ | F | Me | $CH_2CF_3$ | 0 | 159-160 |
| 181 | 1-methylcyclohexyl | $NH_2$ | F | Me | $CH_2CF_3$ | 1 | 89-92 |
| 182 | $CH(CF_3)_2$ | $NH_2$ | F | Me | $CH_2CF_3$ | 0 | 159-161 |
| 183 | $CH(CF_3)_2$ | $NH_2$ | F | Me | $CH_2CF_3$ | 1 | 107-110 |
| 184 | $SCH_2CF_3$ | $NHCH_2C{\equiv}CH$ | F | Me | $CH_2CF_3$ | 0 | 1.5253 |
| 185 | $SCH_2CF_3$ | $NHCH_2C{\equiv}CH$ | F | Me | $CH_2CF_3$ | 1 | 1.5335 |
| 186 | $CF_3$ | NHCOEt | F | Me | $CH_2CF_3$ | 0 | 115-116 |

TABLE 6

| Compound No. | $A^{10}$ | $A^{11}$ | $B^0$ | $B^2$ | R | n | Melting point (°C.) or refractive index ($n_p^{20}$) |
|---|---|---|---|---|---|---|---|
| 187 | $CF_3$ | NHCOEt | F | Me | $CH_2CF_3$ | 1 | 139-141 |
| 189 | $CF_3$ | $NHCOCH_2Cl$ | F | Me | $CH_2CF_3$ | 0 | 72-74 |
| 190 | $CF_3$ | $NHCOCH_2Cl$ | F | Me | $CH_2CF_3$ | 1 | 180-181 |
| 191 | $CF_3$ | $NHCOCF_2Cl$ | F | Me | $CH_2CF_3$ | 0 | |
| 192 | $CF_3$ | $NHCOCF_2Cl$ | F | Me | $CH_2CF_3$ | 1 | 182-184 |
| 193 | $SC_2F_5$ | $NHCH_2C{\equiv}CH$ | F | Me | $CH_2CF_3$ | 0 | 1.5065 |
| 194 | $SC_2F_5$ | $NHCH_2C{\equiv}CH$ | F | Me | $CH_2CF_3$ | 1 | 42-45 |

TABLE 6-continued

| Compound No. | A$^{10}$ | A$^{11}$ | B$^0$ | B$^2$ | R | n | Melting point (° C.) or refractive index (n$_p^{20}$) |
|---|---|---|---|---|---|---|---|
| 195 | S—CH$_2$—(CF$_2$ cyclopropyl) | NH$_2$ | F | Me | CH$_2$CF$_3$ | 0 | 1.5445 |
| 196 | SO—CH$_2$—(CF$_2$ cyclopropyl) | NH$_2$ | F | Me | CH$_2$CF$_3$ | 0 | 150-151 |
| 197 | SO—CH$_2$—(CF$_2$ cyclopropyl) | NH$_2$ | F | Me | CH$_2$CF$_3$ | 1 | 155-167 |
| 198 | SO$_2$—CH$_2$—(CF$_2$ cyclopropyl) | NH$_2$ | F | Me | CH$_2$CF$_3$ | 1 | 174.175 |
| 199 | CF$_3$ | NHCOCHF$_2$ | F | Me | CH$_2$CF$_3$ | 0 | |
| 200 | CF$_3$ | NHCOCHF$_2$ | F | Me | CH$_2$CF$_3$ | 1 | 151-154 |
| 201 | CF$_3$ | NHCONHPr-i | F | Me | CH$_2$CF$_3$ | 0 | 168-171 |
| 202 | CF$_3$ | NHCONHPr-i | F | Me | CH$_2$CF$_3$ | 1 | 168-171 |
| 203 | CF$_3$ | COOMe | F | Me | CH$_2$CF$_3$ | 0 | 92-94 |
| 204 | CF$_3$ | COOMe | F | Me | CH$_2$CF$_3$ | 1 | 143-145 |
| 205 | CF$_3$ | COOEt | F | Me | CH$_2$CF$_3$ | 0 | |
| 206 | CF$_3$ | COOEt | F | Me | CH$_2$CF$_3$ | 1 | 90-92 |
| 207 | CF$_3$ | CONH$_2$ | F | Me | CH$_2$CF$_3$ | 0 | 128-129 |
| 208 | CF$_3$ | CONH$_2$ | F | Me | CH$_2$CF$_3$ | 1 | 202-203 |
| 209 | CF$_3$ | CN | F | Me | CH$_2$CF$_3$ | 0 | 1.4939 |
| 210 | CF$_3$ | CN | F | Me | CH$_2$CF$_3$ | 1 | 95-97 |
| 211 | CF$_3$ | N(Me)COCF$_3$ | F | Me | CH$_2$CF$_3$ | 0 | |
| 212 | CF$_3$ | N(Me)COCF$_3$ | F | Me | CH$_2$CF$_3$ | 1 | 92-94 |
| 213 | CF$_3$ | H | H | CN | Pr | 0 | |
| 214 | CF$_3$ | H | H | CN | Pr | 1 | 134-144 |
| 215 | CF$_3$ | H | H | CN | CH$_2$Pr-c | 0 | 159-160 |
| 216 | CF$_3$ | H | H | CN | CH$_2$Pr-c | 1 | 145-146 |
| 217 | CF$_3$ | H | H | CN | CH$_2$CF$_3$ | 0 | 181-183 |
| 218 | CF$_3$ | H | H | CN | CH$_2$CF$_3$ | 1 | |
| 219 | CF$_3$ | H | H | Me | Pr | 0 | |
| 220 | CF$_3$ | H | H | Me | Pr | 1 | |
| 221 | CF$_3$ | H | H | Me | CH$_2$Pr-c | 0 | |

TABLE 7

| Compound No. | A$^{10}$ | A$^{11}$ | B$^0$ | B$^2$ | R | n | Melting point (° C.) or refractive index (n$_p^{20}$) |
|---|---|---|---|---|---|---|---|
| 222 | CF$_3$ | H | H | Me | CH$_2$Pr-c | 1 | |
| 223 | CF$_3$ | H | H | Me | CH$_2$CF$_3$ | 0 | |
| 224 | CF$_3$ | H | H | Me | CH$_2$CF$_3$ | 1 | 148-150 |
| 225 | CF$_3$ | H | H | CHF$_2$ | Pr | 0 | |
| 226 | CF$_3$ | H | H | CHF$_2$ | Pr | 1 | |
| 227 | CF$_3$ | H | H | CHF$_2$ | CH$_2$Pr-c | 0 | |
| 228 | CF$_3$ | H | H | CHF$_2$ | CH$_2$Pr-c | 1 | |
| 229 | CF$_3$ | H | H | CHF$_2$ | CH$_2$CF$_3$ | 0 | 1.5002 |
| 230 | CF$_3$ | H | H | CHF$_2$ | CH$_2$CF$_3$ | 1 | 1.4982 |
| 231 | CF$_3$ | H | F | CN | Pr | 0 | |
| 232 | CF$_3$ | H | F | CN | Pr | 1 | |
| 233 | CF$_3$ | H | F | CN | CH$_2$Pr-c | 0 | |
| 234 | CF$_3$ | H | F | CN | CH$_2$Pr-c | 1 | |
| 235 | CF$_3$ | H | F | CN | CH$_2$CF$_3$ | 0 | |
| 236 | CF$_3$ | H | F | CN | CH$_2$CF$_3$ | 1 | |
| 237 | CF$_3$ | H | F | Me | Pr | 0 | |
| 238 | CF$_3$ | H | F | Me | Pr | 1 | |
| 239 | CF$_3$ | H | F | Me | CH$_2$Pr-c | 0 | |
| 240 | CF$_3$ | H | F | Me | CH$_2$Pr-c | 1 | |
| 241 | CF$_3$ | H | F | Me | CH$_2$CF$_3$ | 0 | |
| 242 | CF$_3$ | H | F | Me | CH$_2$CF$_3$ | 1 | |

TABLE 7-continued

| Compound No. | $A^{10}$ | $A^{11}$ | $B^0$ | $B^2$ | R | n | Melting point (° C.) or refractive index ($n_p^{20}$) |
|---|---|---|---|---|---|---|---|
| 243 | $CF_3$ | H | F | $CHF_2$ | Pr | 0 | |
| 244 | $CF_3$ | H | F | $CHF_2$ | Pr | 1 | |
| 245 | $CF_3$ | H | F | $CHF_2$ | $CH_2Pr$-c | 0 | |
| 246 | $CF_3$ | H | F | $CHF_2$ | $CH_2Pr$-c | 1 | |
| 247 | $CF_3$ | H | F | $CHF_2$ | $CH_2CF_3$ | 0 | |
| 248 | $CF_3$ | H | F | $CHF_2$ | $CH_2CF_3$ | 1 | |
| 249 | $CF_3$ | H | Cl | CN | Pr | 0 | |
| 250 | $CF_3$ | H | Cl | CN | Pr | 1 | |
| 251 | $CF_3$ | H | Cl | CN | $CH_2Pr$-c | 0 | |
| 252 | $CF_3$ | H | Cl | CN | $CH_2Pr$-c | 1 | |
| 253 | $CF_3$ | H | Cl | CN | $CH_2CF_3$ | 0 | |
| 254 | $CF_3$ | H | Cl | CN | $CH_2CF_3$ | 1 | |
| 255 | $CF_3$ | H | Cl | Me | Pr | 0 | |
| 256 | $CF_3$ | H | Cl | Me | Pr | 1 | |
| 257 | $CF_3$ | H | Cl | Me | $CH_2Pr$-c | 0 | |
| 258 | $CF_3$ | H | Cl | Me | $CH_2Pr$-c | 1 | |
| 259 | $CF_3$ | H | Cl | Me | $CH_2CF_3$ | 0 | |
| 260 | $CF_3$ | H | Cl | Me | $CH_2CF_3$ | 1 | |
| 261 | $CF_3$ | H | Cl | $CHF_2$ | Pr | 0 | |

TABLE 8

| Compound No. | $A^{10}$ | $A^{11}$ | $B^0$ | $B^2$ | R | n | Melting point (° C.) or refractive index ($n_p^{20}$) |
|---|---|---|---|---|---|---|---|
| 262 | $CF_3$ | H | Cl | $CHF_2$ | Pr | 1 | |
| 263 | $CF_3$ | H | Cl | $CHF_2$ | $CH_2Pr$-c | 0 | |
| 264 | $CF_3$ | H | Cl | $CHF_2$ | $CH_2Pr$-c | 1 | |
| 265 | $CF_3$ | H | Cl | $CHF_2$ | $CH_2CF_3$ | 0 | |
| 266 | $CF_3$ | H | Cl | $CHF_2$ | $CH_2CF_3$ | 1 | |
| 267 | $CF_3$ | $NH_2$ | H | CN | Pr | 0 | |
| 268 | $CF_3$ | $NH_2$ | H | CN | Pr | 1 | |
| 269 | $CF_3$ | $NH_2$ | H | CN | $CH_2Pr$-c | 0 | |
| 270 | $CF_3$ | $NH_2$ | H | CN | $CH_2Pr$-c | 1 | |
| 271 | $CF_3$ | $NH_2$ | H | CN | $CH_2CF_3$ | 0 | |
| 272 | $CF_3$ | $NH_2$ | H | CN | $CH_2CF_3$ | 1 | |
| 273 | $CF_3$ | $NH_2$ | H | Me | Pr | 0 | |
| 274 | $CF_3$ | $NH_2$ | H | Me | Pr | 1 | |
| 275 | $CF_3$ | $NH_2$ | H | Me | $CH_2Pr$-c | 0 | |
| 276 | $CF_3$ | $NH_2$ | H | Me | $CH_2Pr$-c | 1 | |
| 277 | $CF_3$ | $NH_2$ | H | Me | $CH_2CF_3$ | 0 | |
| 278 | $CF_3$ | $NH_2$ | H | Me | $CH_2CF_3$ | 1 | |
| 279 | $CF_3$ | $NH_2$ | H | $CHF_2$ | Pr | 0 | |
| 280 | $CF_3$ | $NH_2$ | H | $CHF_2$ | Pr | 1 | |
| 281 | $CF_3$ | $NH_2$ | H | $CHF_2$ | $CH_2Pr$-c | 0 | |
| 282 | $CF_3$ | $NH_2$ | H | $CHF_2$ | $CH_2Pr$-c | 1 | |
| 283 | $CF_3$ | $NH_2$ | H | $CHF_2$ | $CH_2CF_3$ | 0 | |
| 284 | $CF_3$ | $NH_2$ | H | $CHF_2$ | $CH_2CF_3$ | 1 | |
| 285 | $CF_3$ | H | H | CHO | Pr | 0 | |
| 286 | $CF_3$ | H | H | $CH_2OH$ | Pr | 0 | |
| 287 | $CF_3$ | H | H | $CH_2OMe$ | Pr | 0 | |
| 288 | $CF_3$ | H | H | $CH=CH_2$ | Pr | 0 | |
| 289 | $CF_3$ | H | H | $CHBrCHBr_2$ | Pr | 0 | |
| 290 | $CF_3$ | H | H | C≡CH | Pr | 0 | |
| 291 | $CF_3$ | H | H | $CH_2Cl$ | Pr | 0 | |
| 292 | $CF_3$ | H | H | $NO_2$ | Pr | 0 | |
| 293 | $CF_3$ | H | H | $NH_2$ | Pr | 0 | |
| 294 | $CF_3$ | H | H | NHMe | Pr | 0 | |
| 295 | $CF_3$ | H | H | $N(Me)_2$ | Pr | 0 | |
| 296 | $CF_3$ | H | H | NHCOMe | Pr | 0 | |
| 297 | $CF_3$ | H | H | NHCOBu-t | Pr | 0 | |
| 298 | $CF_3$ | H | H | $NHCO_2Me$ | Pr | 0 | |
| 299 | $CF_3$ | H | H | $NHCO_2Bu$-t | Pr | 0 | |
| 300 | $CF_3$ | H | H | $CO_2H$ | Pr | 0 | |
| 301 | $CF_3$ | H | H | $CO_2Me$ | Pr | 0 | |

TABLE 9

| Compound No. | A$^{10}$ | A$^{11}$ | B$^0$ | B$^2$ | R | n | Melting point (° C.) or refractive index (n$_p^{20}$) |
|---|---|---|---|---|---|---|---|
| 302 | CF$_3$ | H | H | Et | Pr | 0 | |
| 303 | CF$_3$ | H | H | CH$_2$F | Pr | 0 | |
| 304 | CF$_3$ | H | H | CF$_3$ | Pr | 0 | |
| 305 | CF$_3$ | H | H | CH=NOH | Pr | 0 | |
| 306 | CF$_3$ | H | H | CH=NOMe | Pr | 0 | |
| 307 | CF$_3$ | H | H | CH(OH)Me | Pr | 0 | |
| 308 | CF$_3$ | H | H | COMe | Pr | 0 | |
| 309 | CF$_3$ | H | H | Cl | Pr | 0 | |
| 310 | CF$_3$ | H | H | Br | Pr | 0 | |
| 311 | CF$_3$ | H | H | I | Pr | 0 | |
| 312 | CF$_3$ | H | H | CHO | Pr | 1 | |
| 313 | CF$_3$ | H | H | CH$_2$OH | Pr | 1 | |
| 314 | CF$_3$ | H | H | CH$_2$OMe | Pr | 1 | |
| 315 | CF$_3$ | H | H | CH=CH$_2$ | Pr | 1 | |
| 316 | CF$_3$ | H | H | CHBrCHBr$_2$ | Pr | 1 | |
| 317 | CF$_3$ | H | H | C≡CH | Pr | 1 | |
| 318 | CF$_3$ | H | H | CH$_2$Cl | Pr | 1 | |
| 319 | CF$_3$ | H | H | NO$_2$ | Pr | 1 | |
| 320 | CF$_3$ | H | H | NH$_2$ | Pr | 1 | |
| 321 | CF$_3$ | H | H | NHMe | Pr | 1 | |
| 322 | CF$_3$ | H | H | N(Me)$_2$ | Pr | 1 | |
| 323 | CF$_3$ | H | H | NHCOMe | Pr | 1 | |
| 324 | CF$_3$ | H | H | NHCOBu-t | Pr | 1 | |
| 325 | CF$_3$ | H | H | NHCO$_2$Me | Pr | 1 | |
| 326 | CF$_3$ | H | H | NHCO$_2$Bu-t | Pr | 1 | |
| 327 | CF$_3$ | H | H | CO$_2$H | Pr | 1 | |
| 328 | CF$_3$ | H | H | CO$_2$Me | Pr | 1 | |
| 329 | CF$_3$ | H | H | Et | Pr | 1 | |
| 330 | CF$_3$ | H | H | CH$_2$F | Pr | 1 | |
| 331 | CF$_3$ | H | H | CF$_3$ | Pr | 1 | |
| 332 | CF$_3$ | H | H | CH=NOH | Pr | 1 | |
| 333 | CF$_3$ | H | H | CH=NOMe | Pr | 1 | |
| 334 | CF$_3$ | H | H | CH(OH)Me | Pr | 1 | |
| 335 | CF$_3$ | H | H | COMe | Pr | 1 | |
| 336 | CF$_3$ | H | H | Cl | Pr | 1 | |
| 337 | CF$_3$ | H | H | Br | Pr | 1 | |
| 338 | CF$_3$ | H | H | I | Pr | 1 | |
| 339 | CF$_3$ | H | H | CHO | CH$_2$Pr-c | 0 | |
| 340 | CF$_3$ | H | H | CH$_2$OH | CH$_2$Pr-c | 0 | |
| 341 | CF$_3$ | H | H | CH$_2$OMe | CH$_2$Pr-c | 0 | |

TABLE 10

| Compound No. | A$^{10}$ | A$^{11}$ | B$^0$ | B$^2$ | R | n | Melting point (° C.) or refractive index (n$_p^{20}$) |
|---|---|---|---|---|---|---|---|
| 342 | CF$_3$ | H | H | CH=CH$_2$ | CH$_2$Pr-c | 0 | |
| 343 | CF$_3$ | H | H | CHBrCHBr$_2$ | CH$_2$Pr-c | 0 | |
| 344 | CF$_3$ | H | H | C≡CH | CH$_2$Pr-c | 0 | |
| 345 | CF$_3$ | H | H | CH$_2$Cl | CH$_2$Pr-c | 0 | |
| 346 | CF$_3$ | H | H | NO$_2$ | CH$_2$Pr-c | 0 | |
| 347 | CF$_3$ | H | H | NH$_2$ | CH$_2$Pr-c | 0 | |
| 348 | CF$_3$ | H | H | NHMe | CH$_2$Pr-c | 0 | |
| 349 | CF$_3$ | H | H | N(Me)$_2$ | CH$_2$Pr-c | 0 | |
| 350 | CF$_3$ | H | H | NHCOMe | CH$_2$Pr-c | 0 | |
| 351 | CF$_3$ | H | H | NHCOBu-t | CH$_2$Pr-c | 0 | |
| 352 | CF$_3$ | H | H | NHCO$_2$Me | CH$_2$Pr-c | 0 | |
| 353 | CF$_3$ | H | H | NHCO$_2$Bu-t | CH$_2$Pr-c | 0 | |
| 354 | CF$_3$ | H | H | CO$_2$H | CH$_2$Pr-c | 0 | |
| 355 | CF$_3$ | H | H | CO$_2$Me | CH$_2$Pr-c | 0 | |
| 356 | CF$_3$ | H | H | Et | CH$_2$Pr-c | 0 | |
| 357 | CF$_3$ | H | H | CH$_2$F | CH$_2$Pr-c | 0 | |
| 358 | CF$_3$ | H | H | CF$_3$ | CH$_2$Pr-c | 0 | |
| 359 | CF$_3$ | H | H | CH=NOH | CH$_2$Pr-c | 0 | |
| 360 | CF$_3$ | H | H | CH=NOMe | CH$_2$Pr-c | 0 | |
| 361 | CF$_3$ | H | H | CH(OH)Me | CH$_2$Pr-c | 0 | |
| 362 | CF$_3$ | H | H | COMe | CH$_2$Pr-c | 0 | |
| 363 | CF$_3$ | H | H | Cl | CH$_2$Pr-c | 0 | |
| 364 | CF$_3$ | H | H | Br | CH$_2$Pr-c | 0 | |
| 365 | CF$_3$ | H | H | I | CH$_2$Pr-c | 0 | |
| 366 | CF$_3$ | H | H | CHO | CH$_2$Pr-c | 1 | |
| 367 | CF$_3$ | H | H | CH$_2$OH | CH$_2$Pr-c | 1 | |

TABLE 10-continued

| Compound No. | $A^{10}$ | $A^{11}$ | $B^0$ | $B^2$ | R | n | Melting point (° C.) or refractive index ($n_p^{20}$) |
|---|---|---|---|---|---|---|---|
| 368 | $CF_3$ | H | H | $CH_2OMe$ | $CH_2Pr$-c | 1 | |
| 369 | $CF_3$ | H | H | $CH=CH_2$ | $CH_2Pr$-c | 1 | |
| 370 | $CF_3$ | H | H | $CHBrCHBr_2$ | $CH_2Pr$-c | 1 | |
| 371 | $CF_3$ | H | H | $C\equiv CH$ | $CH_2Pr$-c | 1 | |
| 372 | $CF_3$ | H | H | $CH_2Cl$ | $CH_2Pr$-c | 1 | |
| 373 | $CF_3$ | H | H | $NO_2$ | $CH_2Pr$-c | 1 | |
| 374 | $CF_3$ | H | H | $NH_2$ | $CH_2Pr$-c | 1 | |
| 375 | $CF_3$ | H | H | NHMe | $CH_2Pr$-c | 1 | |
| 376 | $CF_3$ | H | H | $N(Me)_2$ | $CH_2Pr$-c | 1 | |
| 377 | $CF_3$ | H | H | NHCOMe | $CH_2Pr$-c | 1 | |
| 378 | $CF_3$ | H | H | NHCOBu-t | $CH_2Pr$-c | 1 | |
| 379 | $CF_3$ | H | H | $NHCO_2Me$ | $CH_2Pr$-c | 1 | |
| 380 | $CF_3$ | H | H | $NHCO_2Bu$-t | $CH_2Pr$-c | 1 | |
| 381 | $CF_3$ | H | H | $CO_2H$ | $CH_2Pr$-c | 1 | |

TABLE 11

| Compound No. | $A^{10}$ | $A^{11}$ | $B^0$ | $B^2$ | R | n | Melting point (° C.) or refractive index ($n_p^{20}$) |
|---|---|---|---|---|---|---|---|
| 382 | $CF_3$ | H | H | $CO_2Me$ | $CH_2Pr$-c | 1 | |
| 383 | $CF_3$ | H | H | Et | $CH_2Pr$-c | 1 | |
| 384 | $CF_3$ | H | H | $CH_2F$ | $CH_2Pr$-c | 1 | |
| 385 | $CF_3$ | H | H | $CF_3$ | $CH_2Pr$-c | 1 | |
| 386 | $CF_3$ | H | H | CH=NOH | $CH_2Pr$-c | 1 | |
| 387 | $CF_3$ | H | H | CH=NOMe | $CH_2Pr$-c | 1 | |
| 388 | $CF_3$ | H | H | CH(OH)Me | $CH_2Pr$-c | 1 | |
| 389 | $CF_3$ | H | H | COMe | $CH_2Pr$-c | 1 | |
| 390 | $CF_3$ | H | H | Cl | $CH_2Pr$-c | 1 | |
| 391 | $CF_3$ | H | H | Br | $CH_2Pr$-c | 1 | |
| 392 | $CF_3$ | H | H | I | $CH_2Pr$-c | 1 | |
| 393 | $CF_3$ | H | H | CHO | $CH_2CF_3$ | 0 | 67-68 |
| 394 | $CF_3$ | H | H | $CH_2OH$ | $CH_2CF_3$ | 0 | 96-100 |
| 395 | $CF_3$ | H | H | $CH_2OMe$ | $CH_2CF_3$ | 0 | |
| 396 | $CF_3$ | H | H | $CH=CH_2$ | $CH_2CF_3$ | 0 | |
| 397 | $CF_3$ | H | H | $CHBrCHBr_2$ | $CH_2CF_3$ | 0 | |
| 398 | $CF_3$ | H | H | $C\equiv CH$ | $CH_2CF_3$ | 0 | |
| 399 | $CF_3$ | H | H | $CH_2Cl$ | $CH_2CF_3$ | 0 | |
| 400 | $CF_3$ | H | H | $NO_2$ | $CH_2CF_3$ | 0 | |
| 401 | $CF_3$ | H | H | $NH_2$ | $CH_2CF_3$ | 0 | |
| 402 | $CF_3$ | H | H | NHMe | $CH_2CF_3$ | 0 | |
| 403 | $CF_3$ | H | H | $N(Me)_2$ | $CH_2CF_3$ | 0 | |
| 404 | $CF_3$ | H | H | NHCOMe | $CH_2CF_3$ | 0 | |
| 405 | $CF_3$ | H | H | NHCOBu-t | $CH_2CF_3$ | 0 | |
| 406 | $CF_3$ | H | H | $NHCO_2Me$ | $CH_2CF_3$ | 0 | |
| 407 | $CF_3$ | H | H | $NHCO_2Bu$-t | $CH_2CF_3$ | 0 | |
| 408 | $CF_3$ | H | H | $CO_2H$ | $CH_2CF_3$ | 0 | |
| 409 | $CF_3$ | H | H | $CO_2Me$ | $CH_2CF_3$ | 0 | |
| 410 | $CF_3$ | H | H | Et | $CH_2CF_3$ | 0 | |
| 411 | $CF_3$ | H | H | $CH_2F$ | $CH_2CF_3$ | 0 | 1.5258 |
| 412 | $CF_3$ | H | H | $CF_3$ | $CH_2CF_3$ | 0 | |
| 413 | $CF_3$ | H | H | CH=NOH | $CH_2CF_3$ | 0 | |
| 414 | $CF_3$ | H | H | CH=NOMe | $CH_2CF_3$ | 0 | |
| 415 | $CF_3$ | H | H | CH(OH)Me | $CH_2CF_3$ | 0 | |
| 416 | $CF_3$ | H | H | COMe | $CH_2CF_3$ | 0 | |
| 417 | $CF_3$ | H | H | Cl | $CH_2CF_3$ | 0 | |
| 418 | $CF_3$ | H | H | Br | $CH_2CF_3$ | 0 | |
| 419 | $CF_3$ | H | H | I | $CH_2CF_3$ | 0 | |
| 420 | $CF_3$ | H | H | CHO | $CH_2CF_3$ | 1 | 142-143 |
| 421 | $CF_3$ | H | H | $CH_2OH$ | $CH_2CF_3$ | 1 | |

TABLE 12

| Compound No. | $A^{10}$ | $A^{11}$ | $B^0$ | $B^2$ | R | n | Melting point (° C.) or refractive index ($n_p^{20}$) |
|---|---|---|---|---|---|---|---|
| 422 | $CF_3$ | H | H | $CH_2OMe$ | $CH_2CF_3$ | 1 | |
| 423 | $CF_3$ | H | H | $CH=CH_2$ | $CH_2CF_3$ | 1 | |
| 424 | $CF_3$ | H | H | $CHBrCHBr_2$ | $CH_2CF_3$ | 1 | |

TABLE 12-continued

| Compound No. | $A^{10}$ | $A^{11}$ | $B^0$ | $B^2$ | R | n | Melting point (° C.) or refractive index ($n_p^{20}$) |
|---|---|---|---|---|---|---|---|
| 425 | $CF_3$ | H | H | C≡CH | $CH_2CF_3$ | 1 | |
| 426 | $CF_3$ | H | H | $CH_2Cl$ | $CH_2CF_3$ | 1 | |
| 427 | $CF_3$ | H | H | $NO_2$ | $CH_2CF_3$ | 1 | |
| 428 | $CF_3$ | H | H | $NH_2$ | $CH_2CF_3$ | 1 | |
| 429 | $CF_3$ | H | H | NHMe | $CH_2CF_3$ | 1 | |
| 430 | $CF_3$ | H | H | $N(Me)_2$ | $CH_2CF_3$ | 1 | |
| 431 | $CF_3$ | H | H | NHCOMe | $CH_2CF_3$ | 1 | |
| 432 | $CF_3$ | H | H | NHCOBu-t | $CH_2CF_3$ | 1 | |
| 433 | $CF_3$ | H | H | $NHCO_2Me$ | $CH_2CF_3$ | 1 | |
| 434 | $CF_3$ | H | H | $NHCO_2Bu$-t | $CH_2CF_3$ | 1 | |
| 435 | $CF_3$ | H | H | $CO_2H$ | $CH_2CF_3$ | 1 | |
| 436 | $CF_3$ | H | H | $CO_2Me$ | $CH_2CF_3$ | 1 | |
| 437 | $CF_3$ | H | H | Et | $CH_2CF_3$ | 1 | |
| 438 | $CF_3$ | H | H | $CH_2F$ | $CH_2CF_3$ | 1 | 1.5041 |
| 439 | $CF_3$ | H | H | $CF_3$ | $CH_2CF_3$ | 1 | |
| 440 | $CF_3$ | H | H | CH=NOH | $CH_2CF_3$ | 1 | |
| 441 | $CF_3$ | H | H | CH=NOMe | $CH_2CF_3$ | 1 | |
| 442 | $CF_3$ | H | H | CH(OH)Me | $CH_2CF_3$ | 1 | |
| 443 | $CF_3$ | H | H | COMe | $CH_2CF_3$ | 1 | |
| 444 | $CF_3$ | H | H | Cl | $CH_2CF_3$ | 1 | |
| 445 | $CF_3$ | H | H | Br | $CH_2CF_3$ | 1 | |
| 446 | $CF_3$ | H | H | I | $CH_2CF_3$ | 1 | |
| 447 | $CF_3$ | H | H | Me | Et | 0 | |
| 448 | $CF_3$ | H | H | Me | Pr-i | 0 | |
| 449 | $CF_3$ | H | H | Me | Bu | 0 | |
| 450 | $CF_3$ | H | H | Me | Bu-i | 0 | |
| 461 | $CF_3$ | H | H | Me | Bu-s | 0 | |
| 452 | $CF_3$ | H | H | Me | Bu-t | 0 | |
| 453 | $CF_3$ | H | H | Me | $CH_2CH_2Cl$ | 0 | |
| 454 | $CF_3$ | H | H | Me | Pr-c | 0 | |
| 455 | $CF_3$ | H | H | Me | Bu-c | 0 | |
| 456 | $CF_3$ | H | H | Me | Pen-c | 0 | |
| 457 | $CF_3$ | H | H | Me | Hex-c | 0 | |
| 458 | $CF_3$ | H | H | Me | $CH_2$Bu-c | 0 | |
| 459 | $CF_3$ | H | H | Me | $CH_2$Pen-c | 0 | |
| 460 | $CF_3$ | H | H | Me | $CH_2$-Hex-c | 0 | |
| 461 | $CF_3$ | H | H | Me | Et | 1 | |

TABLE 13

| Compound No. | $A^{10}$ | $A^{11}$ | $B^0$ | $B^2$ | R | n | Melting point (° C.) or refractive index ($n_p^{20}$) |
|---|---|---|---|---|---|---|---|
| 462 | $CF_3$ | H | H | Me | Pr-i | 1 | |
| 463 | $CF_3$ | H | H | Me | Bu | 1 | |
| 464 | $CF_3$ | H | H | Me | Bu-i | 1 | |
| 465 | $CF_3$ | H | H | Me | Bu-s | 1 | |
| 466 | $CF_3$ | H | H | Me | Bu-t | 1 | |
| 467 | $CF_3$ | H | H | Me | $CH_2CH_2Cl$ | 1 | |
| 468 | $CF_3$ | H | H | Me | Pr-c | 1 | |
| 469 | $CF_3$ | H | H | Me | Bu-c | 1 | |
| 470 | $CF_3$ | H | H | Me | Pen-c | 1 | |
| 471 | $CF_3$ | H | H | Me | Hex-c | 1 | |
| 472 | $CF_3$ | H | H | Me | $CH_2$Bu-c | 1 | |
| 473 | $CF_3$ | H | H | Me | $CH_2$Pen-c | 1 | |
| 474 | $CF_3$ | H | H | Me | $CH_2$-Hex-c | 1 | |
| 475 | $CF_3$ | H | H | $CHF_2$ | Et | 0 | |
| 476 | $CF_3$ | H | H | $CHF_2$ | Pr-i | 0 | |
| 477 | $CF_3$ | H | H | $CHF_2$ | Bu | 0 | |
| 478 | $CF_3$ | H | H | $CHF_2$ | Bu-i | 0 | |
| 479 | $CF_3$ | H | H | $CHF_2$ | Bu-s | 0 | |
| 480 | $CF_3$ | H | H | $CHF_2$ | Bu-t | 0 | |
| 481 | $CF_3$ | H | H | $CHF_2$ | $CH_2CH_2Cl$ | 0 | |
| 482 | $CF_3$ | H | H | $CHF_2$ | Pr-c | 0 | |
| 483 | $CF_3$ | H | H | $CHF_2$ | Bu-c | 0 | |
| 484 | $CF_3$ | H | H | $CHF_2$ | Pen-c | 0 | |
| 485 | $CF_3$ | H | H | $CHF_2$ | Hex-c | 0 | |
| 486 | $CF_3$ | H | H | $CHF_2$ | $CH_2$Bu-c | 0 | |
| 487 | $CF_3$ | H | H | $CHF_2$ | $CH_2$Pen-c | 0 | |
| 488 | $CF_3$ | H | H | $CHF_2$ | $CH_2$Hex-c | 0 | |
| 489 | $CF_3$ | H | H | $CHF_2$ | Et | 1 | |

TABLE 13-continued

| Compound No. | $A^{10}$ | $A^{11}$ | $B^0$ | $B^2$ | R | n | Melting point (° C.) or refractive index ($n_D^{20}$) |
|---|---|---|---|---|---|---|---|
| 490 | $CF_3$ | H | H | $CHF_2$ | Pr-i | 1 | |
| 491 | $CF_3$ | H | H | $CHF_2$ | Bu | 1 | |
| 492 | $CF_3$ | H | H | $CHF_2$ | Bu-i | 1 | |
| 493 | $CF_3$ | H | H | $CHF_2$ | Bu-s | 1 | |
| 494 | $CF_3$ | H | H | $CHF_2$ | Bu-t | 1 | |
| 495 | $CF_3$ | H | H | $CHF_2$ | $CH_2CH_2Cl$ | 1 | |
| 496 | $CF_3$ | H | H | $CHF_2$ | Pr-c | 1 | |
| 497 | $CF_3$ | H | H | $CHF_2$ | Bu-c | 1 | |
| 498 | $CF_3$ | H | H | $CHF_2$ | Pen-c | 1 | |
| 499 | $CF_3$ | H | H | $CHF_2$ | Hex-c | 1 | |
| 500 | $CF_3$ | H | H | $CHF_2$ | $CH_2$Bu-c | 1 | |
| 501 | $CF_3$ | H | H | $CHF_2$ | $CH_2$Pen-c | 1 | |

TABLE 14

| Compound No. | $A^{10}$ | $A^{11}$ | $B^0$ | $B^2$ | R | n | Melting point (° C.) or refractive index ($n_D^{20}$) |
|---|---|---|---|---|---|---|---|
| 502 | $CF_3$ | H | H | $CHF_2$ | $CH_2$-Hex-c | 1 | |
| 503 | $CF_3$ | H | F | Cl | $CH_2CF_3$ | 0 | 56-58 |
| 504 | $CF_3$ | H | F | Cl | $CH_2CF_3$ | 1 | 130-132 |
| 505 | $CF_3$ | H | F | Me | $CH_2CF_3$ | 0 | |
| 506 | $CF_3$ | H | F | Me | $CH_2CF_3$ | 1 | |
| 507 | $CF_3$ | H | Cl | Me | $CH_2CF_3$ | 0 | |
| 508 | $CF_3$ | H | Cl | Me | $CH_2CF_3$ | 1 | |
| 509 | $CF_3$ | H | Me | Me | $CH_2CF_3$ | 0 | |
| 510 | $CF_3$ | H | Me | Me | $CH_2CF_3$ | 1 | 149-150 |
| 511 | $CF_3$ | H | Me | Cl | $CH_2CF_3$ | 0 | |
| 512 | $CF_3$ | H | Me | Cl | $CH_2CF_3$ | 1 | |
| 513 | $CF_3$ | H | CN | H | $CH_2CF_3$ | 0 | |
| 514 | $CF_3$ | H | CN | H | $CH_2CF_3$ | 1 | 150-151 |
| 515 | $CF_3$ | H | F | F | $CH_2CF_3$ | 0 | 46-48 |
| 516 | $CF_3$ | H | F | F | $CH_2CF_3$ | 1 | 113-114 |
| 517 | $CF_3$ | H | Cl | Cl | $CH_2CF_3$ | 0 | 70-73 |
| 518 | $CF_3$ | H | Cl | Cl | $CH_2CF_3$ | 1 | 111-112 |

The pesticidal composition of the present invention may contain additive components which are commonly used for agricultural formulations, as the case requires.

Such additive components may, for example, be a carrier such as a solid carrier or a liquid carrier, a surfactant, a binder, an adhesion-imparting agent, a thickener, a coloring agent, an extender, a spreader, an anti-freezing agent, an anti-caking agent, a disintegrating agent and a stabilizing agent.

Further, an antiseptic, plant segments, etc. may be used as additive components, as the case requires. Such additive components may be used alone or in combination as a mixture of two or more of them.

Such additive components will be described.

The solid carrier may, for example, be a natural mineral such as quartz, clay, kaolinite, pyrophillite, sericite, talc, bentonite, acid clay, attapulgite, zeolite or diatomaceous earth; an inorganic salt such as calcium carbonate, ammonium sulfate, sodium sulfate or potassium chloride; synthetic silicic acid or synthetic silicate; an organic solid carrier such as starch, cellulose or plant powder; or a plastic carrier such as polyethylene, polypropylene or polyvinylidene chloride. They may be used alone or in combination as a mixture of two or more of them.

The liquid carrier may, for example, be a monohydric alcohol such as methanol, ethanol, propanol, isopropanol or butanol; a polyhydric alcohol such as ethylene glycol, diethylene glycol, propylene glycol, hexylene glycol, polyethylene glycol, polypropylene glycol or glycerol; a polyhydric alcohol derivative such as propylene type glycol ether; a ketone such as acetone, methyl ethyl ketone, methyl isobutyl ketone, diisobutyl ketone or cyclohexanone; an ether such as ethyl ether, dioxane, cellosolve, dipropyl ether or tetrahydrofuran; an aliphatic hydrocarbon such as normal paraffin, naphthene, isoparaffin, kerosine or mineral oil; an aromatic hydrocarbon such as benzene, toluene, xylene, solvent naphtha or alkyl naphthalene; a halogenated hydrocarbon such as dichloroethane, chloroform or carbon tetrachloride; an ester such as ethyl acetate, diisopropyl phthalate, dibutyl phthalate, dioctyl phthalate or dimethyl adipate; a lactone such as γ-butyrolactone; an amide such as dimethylformamide, diethylformamide, dimethylacetamide or N-alkylpyrrolidinone; a nitrile such as acetonitrile; a sulfur compound such as dimethylsulfoxide; a vegetable oil such as soybean oil, rapeseed oil, cotton oil or castor oil; or water. They may be used alone or in combination as a mixture of two or more of them.

The surfactant is not particularly limited, but it is preferably one to be gelled or swelled in water. It may, for example, be a non-ionic surfactant such as a sorbitan fatty acid ester, a polyoxyethylene sorbitan fatty acid eater, a sucrose fatty acid ester, a polyoxyethylene fatty acid ester, a polyoxyethylene resin acid ester, a polyoxyethylene fatty acid diester, a polyoxyethylene alkyl ether, a polyoxyethylene alkyl phenyl ether, a polyoxyethylene dialkyl phenyl ether, a polyoxyethylene alkyl phenyl ether formalin condensate, a polyoxyethylene polyoxypropylene block copolymer, an alkyl polyoxyethylene polypropylene block polymer ether, a polyoxyethylene alkylamine, a polyoxyethylene fatty acid amide, a polyoxyethylene fatty acid bisphenyl ether, a polyalkylene benzyl phenyl ether, a polyoxyalkylene styryl phenyl ether, an acetylenediol, a polyoxyalkylene-added acetylenediol, a polyoxyethylene ether type silicon, an ester type silicon, a fluorinated surfactant, a polyoxyethylene castor oil or a polyoxyethylene hardened castor oil; an anionic surfactant such as an alkyl sulfate, a polyoxyethylene alkyl ether sulfate, a polyoxyethylene alkyl phenyl ether sulfate, a polyoxyethylene styryl phenyl ether sulfate, an alkyl benzenesulfonate, a lignin sulfonate, an alkylsulfosuccinate, a naphthalenesulfonate, an alkylnaphthalenesulfonate, a salt of a formalin condensate of naphthalenesulfonate, a salt of a formalin condensate of an alkylnaphthalenesulfonate, a fatty acid salt, a polycarboxylic acid salt, an N-methyl-fatty acid sarcosinate, a resin acid salt, a polyoxyethylene alkyl ether phosphate or a polyoxyethylene alkyl phenyl ether phosphate; a cationic surfactant such as a laurylamine hydrochloride, a stearylamine hydrochloride, an oleylamine hydrochloride, a stearylamine acetate, a stearylaminopropylamine acetate, an alkyltrimethylammonium chloride, or an alkyldimethylbenzalkonium chloride; or an amphoteric surfactant such as an amino acid type or a betain type. These surfactants may be used alone or in combination as a mixture of two or more of them.

Further, the binder or adhesion-imparting agent may, for example, be carboxymethylcellulose or its salt, dextrin, water-soluble starch, xanthan gum, guar gum, sucrose, polyvinylpyrrolidone, gum arabic, polyvinyl alcohol, polyvinyl acetate, polysodium acrylate, a polyethylene glycol having an average molecular weight of 6,000 to 20,000, a polyethylene oxide having an average molecular weight of 100,000 to 5,000,000 or a natural phosphatide.

The thickener may, for example, be a water-soluble polymer such as xanthan gum, guar gum, carboxylmethylcellulose, polyvinylpyrrolidone, carboxyvinyl polymer, an acrylic polymer, a starch derivative or polysaccharide; or an inorganic fine powder such as high purity bentonite or white carbon.

The coloring agent may, for example, be an inorganic pigment such as iron oxide, titanium oxide or Prussian blue; or an organic dye such as an arizarin dye, an azo dye or a metal phthalocyanine dye.

The extender may, for example, be a silicon type surfactant, a cellulose powder, dextrin, processed starch, a polyaminocarboxylic acid chelate compound, crosslinked polyvinylpyrrolidone, maleic acid and a styrene, a methacrylic acid copolymer, a half ester of a polymer of a polyhydric alcohol with a dicarboxylic anhydride, or a water-soluble salt of a polystyrene sulfonic acid.

The spreader may, for example, be a surfactant such as sodium dialkylsulfosuccinate, a polyoxyethylene alkyl ether, a polyoxyethylene alkyl phenyl ether or a polyoxyethylene fatty acid ester; paraffin; terpene; a polyamide resin; a polyacrylate; a polyoxyethylene; wax; a polyvinyl alkyl ether; an alkylphenol formalin condensate; or a synthetic resin emulsion.

The anti-freezing agent may, for example, be a polyhydric alcohol such as ethylene glycol, diethylene glycol, propylene glycol or glycerol.

The anti-caking agent may, for example, be starch, alginic acid, a polysaccharide such as mannose or galactose, polyvinylpyrrolidone, white carbon, ester gum or petroleum resin.

The disintegrating agent may, for example, be sodium tripolyphosphate, sodium hexamethaphosphate, stearic acid metal salt, a cellulose powder, dextrin, a methacrylate copolymer, a polyvinylpyrrolidone, a polyaminocarboxylic acid chelate compound, a styrene sulfonate/isobutylene/maleic anhydride copolymer or a starch/polyacrylonitrile graft copolymer.

The stabilizer may, for example, be a drying agent such as zeolite, quick lime or magnesium oxide; an anti-oxidation agent such as a phenol type, an amine type, a sulfur type or a phosphorus type; or an ultraviolet absorber such as a salicylic acid type or a benzophenone type.

The antiseptic may, for example, be potassium sorbate or 1,2-benzthiazolin-3-one.

The plant segments may, for example, be sawdust, coconut shellflower, corn cob or tobacco stem.

The pesticidal composition of the present invention may be formulated into optional formulations such as a liquid formulation, an emulsifiable concentrate, a wettable powder, a water dispersible granule, a dust, an oil miscible solution, a flowable, a granule, a tablet, a jumbo solid formulation, a suspoemulsion, a microcapsule, a paste, a covering agent for seeds, a fumigant, a smoking agent or a Mametsubu (tradename) agent.

The proportion of the total amount of the (component A) and the (component B) in the pesticidal composition of the present invention is usually from about 0.1 to about 80 mass % based on the total amount of the pesticidal composition. Specifically, for example, in the case of a liquid formulation, an emulsifiable concentrate, a wettable powder, a water dispersible granule, a flowable or the like, it is usually properly from about 0.1 to about 80 mass %, preferably from about 10 to about 50 mass %. For example, in the case of an oil miscible solution, a dust or the like, it is properly usually from about 1 to about 50 mass %, preferably from about 0.1 to about 20 mass %. For example, in the case of a granule, a tablet, a jumbo solid formulation or the like, it is properly usually from about 0.5 to 50 mass %, preferably from about 0.5 to about 10 mass %.

In the pesticidal composition of the present invention, the (component A) and the (component B) are preferably contained in a mass ratio of from 1:0.1 to 1:20, more preferably from 1:0.2 to 1:10.

In the pesticidal composition of the present invention, the content of additives other than the above (component A) and the (component B) varies depending on the types or the contents of the (component A) and the (component B), the formulation, or the like, and it is usually from 0.001 to 99.9 mass %, preferably from about 1 to about 99 mass % based on the total amount of the pesticidal composition.

More specifically, based on the total amount of the pesticidal composition, the content of a carrier is usually from 5 to 95 mass %, preferably from 20 to 90 mass %, the content of a surfactant is usually from 0.1 to 30 mass %, preferably from 0.5 to 10 mass %, and the content of other additives is usually from 0.1 to 30 mass %, preferably from 0.5 to 10 mass %.

Further, for the pesticidal composition of the present invention, in addition to the (component A) and the (component B), at least one other agricultural chemical such as another insecticidal component, a miticidal component, a nematicidal component, a synergist, an attractant, a repellent, a herbicidal component, a herbicidal microorganism (such as *Drechslera monoceras, Xanthomonas campestris* pv. *poae*), a fungicidal component, a plant growth modulating component, etc., and a fertilizer, etc. may optionally be blended.

Examples of such insecticidal component, miticidal component, nematicidal component, synergist and fungicidal component are given below.

Insecticidal components, miticidal components and nematicidal components:

Piperonyl butoxide, sesamex sulfoxide, N-(2-ethylhexyl)-bicyclo-(2,2,1)hept-5-ene-2,3-dicarboxylmide, N-declyimidazole, WARF-antiresistant, $CH_3I$ (methyl iodide), t-phenyl-butenone, diethyl maleate and chlorfenetol.

Fungicidal components:

Azaconazole, acibenzolar-S-methyl, azoxystrobin, amisuibrom, isoprothiolane, ipconazole, iprodione, iprovalicarb, imazalil, iprobenfos, iminoctadine-triacetate, imibenconazole, etridiazole, edifenphos, ethaboxam, epoxiconazole, oxadixyl, oxytetracycline, oxycarboxin, oxpoconazole fumarate, octhilinone, oxolinic acid, ofurace, orysastrobin, kasugamycin, captafol, carpropamid, carbendazime, carboxin, chinomethionat, captan, quintozene, guazatine, kresoxim-methyl, chlozolinate, chloroneb, chlorothalonil, cyazofamid, diethofencarb, diclocymet, dichlofluanid, diclomezine, dithianon, diniconazole, zineb, difenoconazole, difenzoquat, cyflufenamid, diflumetorim, cyproconazole, cyprodinil, simeconazole, dimethomorph, cymoxanil, dimoxystrobin, ziram, silthiofam, streptomycin, spiroxamine, zoxamide, dazomet, thiabendazole, thiophanate-methyl, thifluzamide, thiram, tecnazene, tecloftalam, tetraconazole, tebuconazole, dodine, dodemorph, triadimenol, triadimefon, triazoxide, tricyclazole, triticonazole, tridemorph, triflumizole, trifloxystrobin, triforine, tolylfluanid, tolclofos-methyl, nabam, nuarimol, paclobutrazol, validamycin, picoxystrobin, bitertanol, piperalin, hymexazol, pyraclostrobin, pyrazophos, pyrifenox, pyributicarb, pyribencarb, pyrimethanil, pyroquilon, vinclozolin, ferbam, famoxadone, phenazine oxide, fenamidone, fenarimol, fenoxanil, ferimzone, fenpiclonil, fenbuconazole, fenfuram, fenpropidin, fenpropimorph, fenhexamid, folpet, phthalide, bupirimate, fuberidazole, blasticidin-S, furametpyr, furalaxyl, fluazinam, fluoxastrobin, fluopicolide, fluoroimide, fluquinconazole, fludioxonil, flusilazole, flusulfamide, flutolanil, flutriafol, flumorph, proquinazid, prochloraz, procymidone, prothioconazole, propamocarb, propiconazole, propineb, probenazole, bromuconazole, hexaconazole, benalaxyl, benomyl, pefurazoate, penconazole, pencycuron, benthiavalicarb-isopropyl, boscalid, fosetyl, polyoxins, polycarbamate, mandipropamid, mancozeb, maneb, myclobutanil, milneb, methasulfocarb, metalaxyl, metalaxyl-M, metiram, metconazole, metominostrobin, metrafenone, mepanipyrim, mefenoxam, mepronil, penthiopyrad, a silver compound, an inorganic copper compound, an organic copper compound, a sulfur compound, an organic zinc compound, potassium hydrogencarbonate, sodium hydrogencarbonate, fatty acid glyceride, extract from mushroom, *Erwinia*, pseudomonas, *Bacillus, Talaromyces, Trichoderma*, and *Fusarium*.

At the time of practical use of such formulations, they may be used as they are, or they may be diluted to a predetermined concentration with a diluting agent such as water.

Various formulations containing the pesticidal composition of the present invention or their diluted compositions may be applied by conventional methods. Further, the (component A) and the (component B) may be used as mixed at the time of application. Further, the (component A) and the (component B) may be separately applied with an interval of from one day to 30 days for example, preferably from one day to 10 days.

The application examples may, for example, be spreading (e.g. spraying, misting, atomizing, dusting, grain scattering, application into water or box application), soil application (such as soil irrigation, soil incorporation, bed solid incorporation, nursery box application, nursery bed application, root zone application, planting furrow application, row application, side row application), seed surface application (e.g. seed dusting, seed dipping or seed covering), immersion, stem irrigation, stem coating, poisoning, fertilizer incorporation or irrigation water incorporation, but application is not limited thereto.

With respect to the timing of application of a mixed formulation containing the pesticidal composition of the present invention or application by mixing formulations of the respective components, in the case of application to seeds, seed tubers, bulbs or the like, it may be an optional timing prior to planting them, in the case of application to the soil, application at the time of sowing, during raising seedlings or at the time of planting the seedlings is efficient, but application may be possible during growth after the planting, and in the case of foliage application, application during raising seedlings or during growth in a field may be possible.

Further, it is possible to feed domestic animals with a food containing the above active ingredient (the (component A) and the (component B)) to control the outbreak or growth of pests, particularly insect pests, with their excrements. In such a case, it is possible to use a composition substantially consists of the component A and the component B without containing other components.

The mixed formulation containing the pesticidal composition of the present invention or a mixture of formulations of the respective components can control a pest which emerges during raising seedlings by sowing on a culture soil for raising seedlings with which the formulation or the mixture has been incorporated, by temporary planting using the culture soil, or by a solution irrigation or by spraying a granule to the soil during raising seedlings including the sowing.

Further, plants to be treated by the pesticidal composition of the present invention include plants obtained by a conventional plant cultivation method, a biotechnology method such as gene recombination, a combination of such methods, etc.

The application of the pesticidal composition of the present invention is carried out usually at an active ingredient concentration (the total concentration of the (component A) and the (component B)) of from 0.1 to 50,000 ppm, preferably from 1 to 10,000 ppm.

The active ingredient concentration may suitably be changed depending on the type of the formulation, the application method, the purpose of application, the application time, the application site, the degree of outbreak of the pest, etc. For example, aquatic pests can be controlled by applying a chemical solution having the above concentration to the site of the outbreak, and thus, the active ingredient concentration in water is the above concentration or lower.

The amount of application of the active ingredient (the total amount of the (component A) and the (component B)) per unit area is usually from 0.1 to 5,000 g, preferably from 1 to 1,000 g, per hectare, but the amount is not limited thereto.

The pesticidal composition of the present invention is applicable to so-called agricultural insect pests and agricultural pests harmful to agricultural and horticultural crop plants, trees, etc., so-called animal pests parasitic on domestic animals and poultry, so-called hygienic insect pests harmful in the human life environment such as in houses, and mites and nematodes harmful in the similar site, etc.

Specific examples of the insect pests, mites and nematodes to be controlled by the pesticidal composition of the present invention are as follows, but they are not limited thereto.

Pest hemiptera: bugs (HETEROPTERA) such as bean bug (*Riptortus clavatus*), southern green stink bug (*Nezara viridula*), lygus bugs (*Lygus* sp.), hairy chinch bug (*Blissusleucopterus*) and pear lace bug (*Stephanitis nashi*); leafhoppers (Deltocephalinae) such as green rice leafhopper (*Nephotettix*

*cincticeps*) and leafhoppers (*Empoasca* sp., *Erythroneura* sp., *Circulifer* sp.); delphacid planthoppers such as brown rice planthopper (*Nilaparvata lugens*), white-backed planthopper (*Sogatella furcifera*) and small brown planthopper (*Laodelphax striatellus*); jumping plantlice such as Psyllids (*Psylla* sp.); whiteflies such as sweetpotato whitefly (*Bemisiatabaci*) and greenhouse whitefly (*Trialeurodes vaporariorum*); aphides such as grapeleaf louse (*Viteus vitifolii*), green peach aphid (*Myzus persicae*), green apple aphid (*Aphis pomi*), cotton aphid (*Aphis qossypii*), *Aphis fabae*, turnip aphid (*Rhopalosiphum psedobrassicas*), glasshouse-potato aphid (*Aulacorthum solani*) and greenbug (*Schizaphis graminum*); mealy bugs or scales such as Comstock mealybug (*Pseudococcus comstocki*), red wax scale (*Ceroplastes rubens*), San Jose scale (*Comstockaspis perniciosa*) and arrowhead scale (*Unaspis yanonensis*); and assassin bugs (*Rhodinius* sp.).

Pest lepidoptera: tortricids such as oriental tea tortrix (*Homona magnanima*), summer fruit tortrix (*Adoxophyes orana*), tortricids (*Sparganothis pilleriana*), oriental fruit moth (*Grapholitha molesta*), soybean pod borer (*Leguminivoraglycinivorella*), codling moth (*Laspeyresia pomonella*), *Eucosma* sp. and *Lobesia botrana*; Cochylidae such as grape cochylid (*Eupoecillia ambiguella*); bagworm moths such as *Bambalina* sp.; tineids such as European grain moth (*Nemapogon granellus*) and casemaking clothes moth (*Tinea translucens*); lyonetid moths such as *Lyonetiaprunifoliella*; leaf-blotch miners such as apple leafminer (*Phyllonorycter rigoniella*); Phyllocnistidae such as citrus leafminer (*Phyllocnistis citrella*); yponomeutids such as diamondback moth (*Plutella xylostella*) and *Prays citri*; clearwing moths such as grape clearwing moth (*Paranthrene regalis*) and *Synanthedon* sp.; gelechiid moths such as pink bollworm (*Pectinophora gossypiella*), potato tuberworm (*Phthorimaea operculella*) and *Stomopteryx* sp.; Carposinidae such as peach fruit moth (*Carposina niponensis*); slug caterpillarmoths such as oriental moth (*Monema flavescens*); pyralid moths such as Asiatic rice borer (*Chilo suppressalis*), rice leafroller (*Cnaphalocrocis medinalis*), *Ostrinia nubilalis*, oriental corn borer (*Ostrinia furnacalis*), cabbage webworm (*Hellula undalis*), greater wax moth (*Galleriamellonella*), *Elasmopalpus lignosellus* and *Loxostege sticticalis*; whites such as common cabbageworm (*Pieris rapae*); geometrid moths such as mugwort looper (*Ascotis selenaria*); tent caterpillar moths such as tent caterpillar (*Malacosoma neustria*); sphinx moths such as *Manduca sexta*; tussock moths such as tea tussock moth (*Euproctis pseudoconspersa*) and gypsy moth (*Lymantria dispar*); tiger moths such as fall webworm (*Hyphantria cunea*); and owlet moths such as tobacco budworm (*Heliothis virescens*), bollworm (*Helicoverpa zea*), beet armyworm (*Spodoptera exigua*), cotton bollworm (*Helicoverpa armigera*), common cutworm (*Spodoptera litura*), cabbage armyworm (*Mamestra brassicae*), black cutworm (*Agrotis ipsiron*), rice armyworm (*Pseudaletia separata*) and cabbage looper (*Trichoplusia ni*).

Pest coleoptera: chafers such as cupreous chafer (*Anomala cuprea*), Japanese beetle (*Popillia japonica*), soybean beetle (*Anomala rufocuprea*) and *Eutheola rugiceps*; click beetles such as wireworm (*Aqriotes* sp.) and *Conodeus* sp.; ladybirds such as twenty-eight-spotted ladybird (*Epilachna vigintioctopunctata*) and Mexican bean beetle (*Epilachna varivestis*); darkling beetles such as red flour beetle (*Tribolium castaneum*); longicorn beetles such as white-spotted longicorn beetle (*Anoplophora malasiaca*) and pine sawyer (*Monochamus alternatus*); seed beetles such as bean weevil (*Acanthoscelides obtectus*) and adzuki bean weevil (*Callosobruchus chinensis*); leaf beetles such as colorado potato beetle (*Leptinotarsa decemlineata*), corn rootworm (*Diabrotica* sp.), rice leaf beetle (*Oulema oryzae*), beet flea beetle (*Chaetocnema concinna*), *Phaedon cochlearias*, *Oulema melanopus* and *Dicladispa armigera*; Apionidae such as *Apion godmani*; weevils such as rice water weevil (*Lissorhoptrus oryzophilus*) and cotton boll weevil (*Anthonomus grandis*); Rhynchophoridae such as maize weevil (*Sitophilus zeamais*); bark beetles; dermestid beetles; and drugstore beetles.

Pet diptera: rice crane fly (*Tipra ano*), rice midge (*Tanytarsus oryzae*), gall midge (*Orseolia oryzae*), medfly (*Ceratitis capitata*), rice leafminer (*Hydrellia griseola*), cherry drosophila (*Drosophila suzukii*), frit fly (*Oscinella frit*), rice stem maggot (*Chlorops oryzae*), French bean miner (*Ophiomyia phaseoli*), legume leafminer (*Liriomyza trifolii*), spinach leafminer (*Pegomya hyoscyami*), seedcorn maggot (*Hylemiaplatura*), sorghum fly (*Atherigona soccata*), muscid fly (*Musca domestica*), horse bot-flies (*Gastrophilus* sp.), stable flies (*Stomoxys* sp.), yellow fever mosquito (*Aedes aegypti*), northern house mosquito (*Culex pipiens*), malaria mosquito (*Anopheles slnensis*) and *Culex tritaeniorhynchus*.

Pest hymenoptera: stem sawflies (*Cephus* sp.); eurytomids (*Harmolita* sp.); cabbage sawflies (*Athalia* sp.), hornets (*Vespa* sp.) and fire ants.

Pest orthoptera: German cockroach (*Blatella germanica*), American cockroach (*Periplaneta americana*), African mole cricket (*Gryllotalpa africana*), Asiatic locust (*Locustamigratoria migratoriodes*), and *Melanoplussanguinipes*.

Pest isoptera: termites (*Reticulitermessperatus*) and Formosan subterranean termite (*Coptotermes formosanus*).

Pest thysanopetra: yellow tea thrips (*Scirtothrips dorsalis*), melon thrips (*Thrips palmi*), greenhouse thrips (*Heliothrips haemorrholidalis*), western flower thrips (*Frankliniella occidentalis*) and rice aculeated thrips (*Haplothrips aculeatus*).

Mites: two-spotted spider mite (*Tetranychus urticae*), Kanzawa spider mite (*Tetranychus kanzawai*), citrus red mite (*Panonychus citri*), European red mite (*Panonychusulmi*), yellow spider mite (*Eotetranychus carpini*), Texas citrus mite (*Eotetranychus banksi*), citrus rust mite (*Phyllocoptruta oleivora*), broad mite (*Polyphagotarsonemus latus*), false spider mites (*Brevipalpus* sp.), bulb mite (*Rhizoglyphus robini*) and mold mite (*Tyrophagus putrescentiae*).

Plant-parasitic nematodes: southern root-knot nematode (*Meloidogyne incognita*), root-lesion nematode (*Pratylenchus* sp.), soybean cyst nematode (*Heterodera glycines*), rice white-tip nematode (*Aphelenchoides besseyi*), pine wood nematode (*Bursaphelenchus xylophilus*), *Radopholus similis*, stem and bulb nematode (*Ditylenchus dipsaci*), citrus nematode (*Tylenchulus semipenetrans*), *Globodera* spp., root-knot nematodes (*Meloidogyne* spp.), *Aphelenchoides* spp., *Longidorus* spp., *Xiphinema* spp., *Trichodorus* spp. and *Bursaphelenchus* spp.

Other pests, unfavorable animals, insanitary insects, and parasites: gastropods (*Gastropoda*) such as apple snails (*Pomacea canaliculata*), slugs (*Incilaria* sp.) and giant African snail (*Achatina fulica*); isopods (*Isopoda*) such as pillbug (*Armadillidium* sp.), sow bug and centipede; booklice such as *Liposcelis* sp.; silverfish such as *Ctenolepisma* sp.; fleas such as *Pulex* sp. and *Ctenocephalides* sp.; bird lice such as *Trichodectes* sp.; bed bugs such as *Cimex* sp.; aminal-parasitic mites such as *Boophilus microplus* and *Haemaphysalis longicornis* and Epidermoptidae.

The pesticidal composition of the present invention has controlling effects also against the above pest insects which show resistance to the existing pesticides, particularly against pest insects which show resistance to organophosphorus compounds, carbamate compounds, synthetic pyrethroid compounds, acylurea compounds or conventional insecticides.

Now, the present invention will be described in detail with reference to typical Examples and Test Examples, but the present invention is by no means restricted thereto.

The types of the (component A), the (component B) and adjuvants, and their blend ratios are not limited to the following, and various changes are possible within a wide range. In the following description, part(s) means mass %.

EXAMPLES

Formulation Example 1

Emulsifiable Concentrate

| | |
|---|---|
| Compound No. (6) | 5 parts |
| Known compound flubendiamide | 30 parts |
| Cyclohexanone | 20 parts |
| Polyoxyethylene alkyl aryl ether | 11 parts |
| Calcium alkylbenzenesulfonate | 4 parts |
| Methyl naphthalene | 30 parts |

The above compounds were uniformly dissolved to obtain an emulsifiable concentrate.

Formulation Example 2

Emulsifiable Concentrate

| | |
|---|---|
| Compound No. (6) | 4 parts |
| Known compound pyridalyl | 20 parts |
| Cyclohexanone | 20 parts |
| Polyoxyethylene alkyl aryl ether | 11 parts |
| Calcium alkylbenzenesulfonate | 4 parts |
| Methyl naphthalene | 41 parts |

The above compounds were uniformly dissolved to obtain an emulsifiable concentrate.

Formulation Example 3

Wettable Powder

| | |
|---|---|
| Compound No. (6) | 1 part |
| Known compound pyridalyl | 10 parts |
| Sodium salt of naphthalenesulfonic acid formalin condensate | 0.5 part |
| Polyoxyethylene alkyl aryl ether | 0.5 part |
| Diatomaceous earth | 24 parts |
| Clay | 64 parts |

The above compounds were uniformly mixed and pulverized to obtain a wettable powder.

Formulation Example 4

Wettable Powder

| | |
|---|---|
| Compound No. (6) | 0.4 part |
| Known compound flubendiamide | 20 parts |
| Sodium salt of naphthalenesulfonic acid formalin condensate | 0.5 part |
| Polyoxyethylene alkyl aryl ether | 0.5 part |
| Diatomaceous earth | 24 parts |
| Clay | 54.6 parts |

The above compounds were uniformly mixed and pulverized to obtain a wettable powder.

Formulation Example 5

Dust

| | |
|---|---|
| Compound No. (6) | 0.1 part |
| Known compound ethiprole | 0.4 part |
| Diatomaceous earth | 5 parts |
| Clay | 94.5 parts |

The above compounds were uniformly mixed and pulverized to obtain a dust.

Formulation Example 6

Granule

| | |
|---|---|
| Compound No. (6) | 0.5 part |
| Known compound cadusafos | 2.5 parts |
| Sodium lauryl alcohol sulfate | 2 parts |
| Sodium lignin sulfonate | 5 parts |
| Carboxymethyl cellulose | 2 parts |
| Clay | 88 parts |

The above compounds were uniformly mixed and pulverized. To 100 parts by mass of the mixture, 20 parts by mass of water was added, followed by kneading, and the kneaded product was formed into granules of 14 to 32 mesh by an extrusion granulator, which were dried to obtain a granule.

Now, the effect of the pesticidal composition comprising the compound of the present invention as an active ingredient will be described with reference to Test Examples.

Test Example 1

Miticidal Test on Two-Spotted Spider Mites

Each of the compound 6, flubendiamide, and a mixture of the compound 6 and flubendiamide was formulated into a wettable powder in accordance with Formulation Example 2. The respective formulations were diluted with water to an active ingredient concentration as identified in Table 15, and to the respective solutions, a spreader (KUMITEN manufactured by Kumiai Chemical Industry Co., Ltd.) was added at a concentration of 0.05% of the entire amount. Soybean seedlings which had been inoculated with imago two-spotted spider mites were dipped in each of the resulting solutions and dried in air. The seedlings were placed in a thermostatic chamber at 25° C. for 13 days, and the mite survivors were counted for calculation of the miticidal value by using Equation 2. The test was carried out by one series system. The results of this test are shown in Table 15. The predictive value in the Table was calculated based on the Colby formula (S. R. Colby (Weeds 15 (1967), 20-22) of Equation 1.

$$E = X + Y - \frac{X \times Y}{100} \quad \text{Equation 1}$$

wherein X, Y and E are the following values.

X: The miticidal value of the component A at a predetermined concentration.

Y: The miticidal value of the component B at a predetermined concentration.

E: Predictive value (theoretical expected value) of the component A and the component B in combination at the respective predetermined concentrations.

$$\text{Miticidal value} = \left(1 - \frac{\substack{\text{Mites before treatment} \\ \text{in non-treated area}}}{\substack{\text{Mites before treatment} \\ \text{in treated area}}} \times \frac{\substack{\text{Mites on the date of} \\ \text{observation in treated area}}}{\substack{\text{Mites on the date of} \\ \text{observation in non-treated area}}}\right) \times 100 \quad \text{Equation 2}$$

When the practical miticidal value of the insecticide exceeds E (predictive value), a synergistic effect is obtained.

TABLE 15

| Compound | Concentration (ppm) | Miticidal value |
|---|---|---|
| Compound No. 6 | 1.0 | 89 |
| Flubendiamide | 50.0 | 13 |
| Compound No. 6 + Flubendiamide | 1.0 + 50.0 | 100 |
| Compound No. 6 + Flubendiamide | 1.0 + 50.0 | 90 (Predictive value) |

Test Example 2

Miticidal Test on Two-Spotted Spider Mites

Each of the compound 6, tebufenozide, and a mixture of the compound 6 and tebufenozide was formulated into a wettable powder in accordance with Formulation Example 2. The respective formulations were diluted with water to an active ingredient concentration as identified in Table 16, and to the respective solutions, a spreader (KUMITEN manufactured by Kumiai Chemical Industry Co., Ltd.) was added at a concentration of 0.05% of the entire amount. Soybean seedlings which had been inoculated with imago two-spotted spider mites were dipped in each of the resulting solutions and dried in air. The seedlings were placed in a thermostatic chamber at 25° C. for 13 days, and the mite survivors were counted for calculation of the miticidal value by using Equation 2. The test was carried out by one series system. The results of this test are shown in Table 16. The theoretical value in the Table was calculated based on the Colby formula of Equation 1.

TABLE 16

| Compound | Concentration (ppm) | Miticidal value |
|---|---|---|
| Compound No. 6 | 1.0 | 89 |
| Tebufenozide | 100.0 | 3 |
| Compound No. 6 + Tebufenozide | 1.0 + 100.0 | 100 |
| Compound No. 6 + Tebufenozide | 1.0 + 100.0 | 89 (Predictive value) |

Test Example 3

Insecticidal Test on Cotton Aphid

Each of the compound 6, pyridalyl, and a mixture of the compound 6 and pyridalyl was formulated into a wettable powder in accordance with Formulation Example 2. The respective formulations were diluted with water to an active ingredient concentration as identified in Table 17, and to the respective solutions, a spreader (KUMITEN manufactured by Kumiai Chemical Industry Co., Ltd.) was added at a concentration of 0.05% of the entire amount. The root zone of cucumber seedlings which had been inoculated with larvae of cotton aphid were irrigated with 5 mL of each of the solutions. The treated seedlings were placed in a thermostatic chamber at 25° C. for 3 days, and the survivors were counted for calculation of the insecticidal degree by Equation 3. The test was carried out by two series system. The results of this test are shown in Table 17. The predictive value in the Table was calculated based on the Colby formula of Equation 1.

$$\text{Insecticidal degree } (\%) = \left(1 - \frac{\text{Survivors}}{\text{Larvae to be tested}}\right) \times 100 \quad \text{Equation 3}$$

TABLE 17

| Compound | Concentration (ppm) | Miticidal value |
|---|---|---|
| Compound No. 6 | 20.0 | 90 |
| Pyridalyl | 100.0 | 10 |
| Compound No. 6 + Pyridalyl | 20.0 + 100.0 | 100 |
| Compound No. 6 + Pyridalyl | 20.0 + 100.0 | 91 (Predictive value) |

INDUSTRIAL APPLICABILITY

The pesticidal composition of the present invention exhibits a satisfactory pesticidal effect even at a low dose, its pesticidal effect will be achieved at an earlier stage and will be retained for a longer time, and it exhibits excellent pesticidal effects against various pests, especially agricultural and horticultural pests such as mites, pest lepidopterans, pest hemipterans and pest coleopteran, and it is thereby agriculturally and horticulturally useful.

The entire disclosure of Japanese Patent Application No. 2007-209387 filed on Aug. 10, 2007 including specification, claims and summary is incorporated herein by reference in its entirety.

The invention claimed is:

1. A pesticidal composition, comprising synergistically effective amounts of:

(A) at least one 1-arylphenyl sulfide derivative represented by the formula [I]:

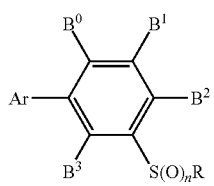

[I]

wherein
- R is a $C_2$-$C_6$ alkyl group which may be mono-substituted or poly-substituted by a halogen atom or a cyano group, a $C_2$-$C_6$ alkenyl group which may be mono-substituted or poly-substituted by a halogen atom or a cyano group, a $C_2$-$C_6$ alkynyl group which may be mono-substituted or poly-substituted by a halogen atom or a cyano group, a $C_3$-$C_6$ cycloalkyl group which may be mono-substituted or poly-substituted by a halogen atom or a cyano group or a $C_4$-$C_9$ cycloalkylalkyl group which may be mono-substituted or poly-substituted by a halogen atom or a cyano group,
- n is an integer of from 0 to 2,
- Ar is a group represented by the formula Ar-4:

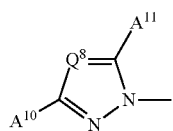

[Ar-4]

wherein
- $Q^8$ is a nitrogen atom,
- $B^0$ is a hydrogen atom, a halogen atom, an amino group, a cyano group, a nitro group, a $C_1$-$C_6$ alkyl group, a $C_1$-$C_4$ haloalkyl group, a $C_1$-$C_6$ alkylthio group which may be mono-substituted or poly-substituted by a halogen atom or a $C_1$-$C_6$ alkoxy group,
- $B^1$, $B^2$ and $B^3$ are each, independently, a hydrogen atom, a halogen atom, a cyano group, a nitro group, a $C_1$-$C_6$ alkyl group which may be mono-substituted or poly-substituted by a halogen atom, a hydroxy group, a cyano group, a $C_2$-$C_7$ alkoxycarbonyl group or a $C_1$-$C_6$ alkoxy group, a $C_2$-$C_6$ alkenyl group which may be mono-substituted or poly-substituted by a halogen atom or a cyano group, a $C_2$-$C_6$ alkynyl group which may be mono-substituted or poly-substituted by a halogen atom or a cyano group, a $C_1$-$C_6$ alkoxy group which may be mono-substituted or poly-substituted by a halogen atom, a cyano group, a $C_2$-$C_5$ alkoxycarbonyl group or a $C_1$-$C_3$ alkoxy group, a $C_1$-$C_6$ alkylthio group which may be mono-substituted or poly-substituted by a halogen atom or a $C_1$-$C_3$ alkoxy group, a $C_1$-$C_6$ alkylsulfinyl group which may be mono-substituted or poly-substituted by a halogen atom or a $C_1$-$C_3$ alkoxy group, a $C_1$-$C_6$ alkylsulfonyl group which may be mono-substituted or poly-substituted by a halogen atom or a $C_1$-$C_3$ alkoxy group, a $C_1$-$C_7$ acyl group, a $C_2$-$C_5$ haloalkylcarbonyl group, a carboxy group, a $C_2$-$C_7$ alkoxycarbonyl group or a —$NR^1R^2$ group,
- $R^1$ and $R^2$ are each, independently, a hydrogen atom, a $C_1$-$C_6$ alkyl group which may be mono-substituted or poly-substituted by a halogen atom, a cyano group, a hydroxy group, a $C_1$-$C_6$ alkoxy group or a $C_1$-$C_6$ alkylthio group, a $C_2$-$C_6$ alkenyl group which may be mono-substituted or poly-substituted by a halogen atom or a cyano group, a $C_2$-$C_6$ alkynyl group which may be mono-substituted or poly-substituted by a halogen atom or a cyano group, a $C_1$-$C_7$ acyl group or a $C_2$-$C_7$ alkoxycarbonyl group,
- $A^{10}$ is a hydrogen atom, a carboxy group, a $C_2$-$C_7$ alkoxycarbonyl group, a halogen atom, a $C_1$-$C_6$ alkyl group which may be mono-substituted or poly-substituted by a halogen atom, a hydroxy group, a cyano group, a $C_2$-$C_7$ alkoxycarbonyl group or a $C_1$-$C_6$ alkoxy group, a $C_3$-$C_8$ cycloalkyl group which may be mono-substituted or poly-substituted by an alkyl group, a halogen atom, a cyano group or a $C_1$-$C_6$ alkoxy group, a $C_2$-$C_6$ alkenyl group which may be mono-substituted or poly-substituted by a halogen atom or a cyano group, a $C_2$-$C_6$ alkynyl group which may be mono-substituted or poly-substituted by a halogen atom or a cyano group, a $C_1$-$C_6$ alkoxy group which may be mono-substituted or poly-substituted by a halogen atom, a cyano group, a $C_2$-$C_5$ alkoxycarbonyl group or a $C_1$-$C_3$ alkoxy group, a $C_1$-$C_6$ alkylthio group which may be mono-substituted or poly-substituted by a halogen atom, a $C_1$-$C_3$ alkoxy group, a $C_3$-$C_8$ cycloalkyl group which may be substituted by a halogen atom, or a cyano group, a $C_1$-$C_6$ alkylsulfinyl group which may be mono-substituted or poly-substituted by a halogen atom, a $C_1$-$C_3$ alkoxy group, a $C_3$-$C_8$ cycloalkyl group which may be substituted by a halogen atom, or a cyano group, a $C_1$-$C_6$ alkylsulfonyl group which may be mono-substituted or poly-substituted by a halogen atom, a $C_1$-$C_3$ alkoxy group or a $C_3$-$C_8$ cycloalkyl group which may be substituted by a halogen atom, a $C_2$-$C_6$ alkynylthio group which may be mono-substituted or poly-substituted by a halogen atom, a $C_1$-$C_3$ alkoxy group or a cyano group, a $C_2$-$C_6$ alkynylsulfinyl group which may be mono-substituted or poly-substituted by a halogen atom, a $C_1$-$C_3$ alkoxy group or a cyano group, a $C_1$-$C_7$ acyl group or a $C_2$-$C_5$ haloalkylcarbonyl group,
- $A^{11}$ is a hydrogen atom, a halogen atom, a cyano group, a nitro group, a $C_1$-$C_6$ alkyl group, a $C_1$-$C_4$ haloalkyl group, a $C_1$-$C_6$ alkylthio group which may be mono-substituted or poly-substituted by a halogen atom, a $C_1$-$C_6$ alkoxy group, a —$N=CR^3R^4$ group, a —$N=C(NR^4R^{5'})NR^4R^5$ group, a —$N(SO_2R^4)R^5$ group, a —$N(OR^5)R^{5'}$ group, a —$C(=O)OR^4$ group, a —$C(=O)NR^4R^5$ group, a —$SO_2NR^4R^5$ group, a —$NR^4R^5$ group, a —$N(COR^4)R^5$ group or a —$N(COOR^4)R^5$ group,
- $R^3$ is a hydrogen atom, a $C_1$-$C_6$ alkyl group which may be mono-substituted or poly-substituted by a halogen atom, a hydroxy group, a cyano group, a $C_2$-$C_7$ alkoxycarbonyl group or a $C_1$-$C_6$ alkoxy group, a $C_3$-$C_6$ alkenyl group which may be mono-substituted or poly-substituted by a halogen atom or a cyano group, a $C_3$-$C_6$ alkynyl group which may be mono-substituted or poly-substituted by a halogen atom or a cyano group, a $C_3$-$C_6$ cycloalkyl group which may be mono-substituted or poly-substituted by a halogen atom, a hydroxy group, a cyano group, a $C_2$-$C_7$ alkoxycarbonyl group or a $C_1$-$C_6$ alkoxy group, an arylalkyl group which may be mono-substituted or poly-substituted by a halogen atom, a cyano group, a $C_1$-$C_6$ alkyl group, a $C_1$-$C_6$ haloalkyl group, a $C_2$-$C_7$ alkoxycarbonyl group or a $C_1$-$C_6$ alkoxy group, a heteroarylalkyl group which may be mono-substituted or poly-substituted by a halogen atom, a cyano group, a $C_1$-$C_6$ alkyl group, a $C_1$-$C_6$ haloalkyl group, a $C_2$-$C_7$ alkoxycarbonyl group or a $C_1$-$C_6$ alkoxy group, an aryl group which may be mono-substituted or poly-substituted by a halogen atom, a cyano group, a $C_1$-$C_6$ alkyl group, a $C_1$-$C_6$ haloalkyl group, a $C_2$-$C_7$ alkoxycarbonyl group, a $C_1$-$C_6$ alkoxy group or a hydroxy group, a heteroaryl group which may be mono-substituted or poly-substituted by a halogen atom, a cyano group, a $C_1$-$C_6$ alkyl group, a $C_1$-$C_6$ haloalkyl group, a $C_2$-$C_7$ alkoxycarbonyl group or a $C_1$-$C_6$ alkoxy group, a $C_1$-$C_6$ alkoxy group, a $C_1$-$C_6$ alkylthio group, an amino group, a $C_1$-$C_6$ monoalkylamino group or a $C_2$-$C_{12}$ dialkylamino group, $R^4$ and $R^{4'}$ are each, independently, a hydrogen atom, a $C_1$-$C_6$ alkyl group which may be mono-substituted or poly-substituted by a halogen atom, a hydroxy group, a cyano group, a $C_2$-$C_7$ alkoxycarbonyl group or a $C_1$-$C_6$ alkoxy group, a $C_3$-$C_6$ alkenyl group which may be mono-substituted or poly-substituted by a halogen atom or a cyano group, a $C_3$-$C_6$ alkynyl group which may be mono-substituted or poly-substituted by a halogen atom or a cyano group, a $C_3$-$C_6$ cycloalkyl group which may be mono-substituted or poly-substituted by a halogen atom, a hydroxy group, a cyano group, a $C_2$-$C_7$ alkoxycarbonyl group or a $C_1$-$C_6$ alkoxy group, an amino group, a $C_1$-$C_6$ monoalkylamino group, a $C_2$-$C_{12}$ dialkylamino group, an arylalkyl group which may be mono-substituted or poly-substituted by a halogen atom, a cyano group, a $C_1$-$C_6$ alkyl group, a $C_1$-$C_6$ haloalkyl group, a $C_2$-$C_7$ alkoxycarbonyl group or a $C_1$-$C_6$ alkoxy group, a heteroarylalkyl group which may be mono-substituted or poly-substituted by a halogen atom, a cyano group, a $C_1$-$C_6$ alkyl group, a $C_1$-$C_6$ haloalkyl group, a $C_2$-$C_7$ alkoxycarbonyl group or a $C_1$-$C_6$ alkoxy group, an aryl group which may be mono-substituted or poly-substituted by a halogen atom, a cyano group, a $C_1$-$C_6$ alkyl group, a $C_1$-$C_6$ haloalkyl group, a $C_2$-$C_7$ alkoxycarbonyl group or a $C_1$-$C_6$ alkoxy group or a heteroaryl group which may be mono-substituted or poly-substituted by a halogen atom, a cyano group, a $C_1$-$C_6$ alkyl group, a $C_1$-$C_6$ haloalkyl group, a $C_2$-$C_7$ alkoxycarbonyl group or a $C_1$-$C_6$ alkoxy group, and $R^5$ and $R^{5'}$ are each, independently, a hydrogen atom, a $C_1$-$C_6$ alkyl group which may be mono-substituted or poly-substituted by a halogen atom, a hydroxy group, a cyano group, a $C_2$-$C_7$ alkoxycarbonyl group or a $C_1$-$C_6$ alkoxy group, a $C_3$-$C_6$ alkenyl group which may be mono-substituted or poly-substituted by a halogen atom or a cyano group, a $C_3$-$C_6$ alkynyl group which may be mono-substituted or poly-substituted by a halogen atom or a cyano group or a $C_3$-$C_6$ cycloalkyl group which may be mono-substituted or poly-substituted by a halogen atom, a hydroxy group, a cyano group, a $C_2$-$C_7$ alkoxycarbonyl group or a $C_1$-$C_6$ alkoxy group; and (B) flonicamid.

2. The pesticidal composition of claim 1, wherein R is a $C_2$-$C_6$ alkyl group, which may be mono-substituted or poly-substituted by a halogen atom or a $C_4$-$C_9$ cycloalkylalkyl group, which may be mono-substituted or poly-substituted by a halogen atom.

3. The pesticidal composition of claim 1, wherein R is a trifluoroethyl group, n is 0 or 1, $A^{10}$ is a $C_1$-$C_6$ alkyl group, which may be mono-substituted or poly-substituted by a halogen atom or a cyano group, a $C_1$-$C_6$ alkylthio group, which may be mono-substituted or poly-substituted by a halogen atom or a $C_1$-$C_6$ alkylsulfinyl group, which may be mono-substituted or poly-substituted by a halogen atom or a $C_1$-$C_3$ alkoxy group group, $A^{11}$ is a hydrogen atom, a —$NR^4R^5$ group or a —$N(COR^4)R^5$ group, $R^4$ and $R^5$ are each, independently, a hydrogen atom, a $C_1$-$C_6$ alkylamino group, a $C_1$-$C_6$ alkyl group, which may be mono-substituted or poly-substituted by a halogen atom or a cyano group or a $C_3$-$C_6$ alkynyl group, which may be mono-substituted or poly-substituted by a halogen atom or a cyano group, and $B^0$ is a hydrogen atom, a halogen atom or a methyl group, and $B^2$ is a cyano group or a $C_1$-$C_6$ alkyl group, which may be mono-substituted or poly-substituted by a halogen atom.

4. The pesticidal composition of claim 1,
R is a trifluoroethyl group,
n is 0 or 1,
$A^{10}$ is a $C_1$-$C_6$ alkyl group, which may be mono-substituted or poly-substituted by a halogen atom or a cyano group, a $C_1$-$C_6$ alkylthio group, which may be mono-substituted or poly-substituted by a halogen atom or a $C_1$-$C_6$ alkylsulfinyl group, which may be mono-substituted or poly-substituted by a halogen atom or a $C_1$-$C_3$ alkoxy group,
$A^{11}$ is —$NH_2$,
$B^0$ is a halogen atom or a methyl group, and
$B^2$ is a cyano group or a $C_1$-$C_6$ alkyl group, which may be mono-substituted or poly-substituted by a halogen atom.

5. The pesticidal composition according to claim 1, wherein
$A^{10}$ is —$CF_3$,
$A^{11}$ is —$NH_2$,
$B^0$ is —F,
$B^1$ is a hydrogen atom,
$B^2$ is a methyl group,
$B^3$ is a hydrogen atom, and
R is —$CH_2CF_3$.

6. The pesticidal composition according to claim 5, wherein n is 1.

7. The pesticidal composition according to claim 1, wherein
$A^{10}$ is $S(O)CHF_2$,
$A^{11}$ is —$NH_2$,
$B^0$ is —F,
$B^2$ is a methyl group,
R is —$CH_2CF_3$, and
n is 1.

8. The pesticidal composition according to claim 1, wherein n is 0.

9. A method for controlling a pest, which comprises directly spraying the pesticidal composition of claim 1 to a surface of a plant or to the pest.

10. A method for controlling a pest, which comprises applying the pesticidal composition of claim 1 directly to the soil or directly to seeds, seed tubers or bulbs or to the vicinity thereof.

* * * * *